United States Patent [19]

Leitch et al.

[11] Patent Number: 5,753,216
[45] Date of Patent: May 19, 1998

[54] HAIR CARE COMPOSITIONS HAVING STYLING/CONDITIONING AGENT AND PLASTICIZER

[75] Inventors: Steven Hilary Leitch, Maineville; Lisa Jo Bartz; Kathleen Brown Fish, both of Cincinnati, all of Ohio

[73] Assignee: The Procter & Gamble Company, Cincinnati, Ohio

[21] Appl. No.: 203,723

[22] Filed: Feb. 28, 1994

Related U.S. Application Data

[63] Continuation of Ser. No. 26,144, Mar. 2, 1993, abandoned, which is a continuation of Ser. No. 671,578, Mar. 19, 1991, abandoned.

[51] Int. Cl.⁶ .............................................. A61K 7/075
[52] U.S. Cl. .................. 424/70.12; 424/70.1; 424/70.27; 424/70.28
[58] Field of Search .................... 424/71, 78.18, 424/78.31, 78.37, 78.38, 70.1, 70.12, 70.27, 70.28; 514/772.3–772.7

[56] References Cited

U.S. PATENT DOCUMENTS

| | | | |
|---|---|---|---|
| 4,871,529 | 10/1989 | Sramek | 424/71 |
| 4,981,902 | 1/1991 | Mitra et al. | 524/547 |
| 4,988,506 | 1/1991 | Mitra et al. | 424/78 |
| 5,019,377 | 5/1991 | Torgerson | 424/70 |
| 5,061,481 | 10/1991 | Suzuki et al. | 424/63 |
| 5,100,657 | 3/1992 | Ansher-Jackson et al. | 424/70 |
| 5,100,658 | 3/1992 | Bolich et al. | 424/70 |
| 5,104,642 | 4/1992 | Wells et al. | 424/47 |
| 5,104,646 | 4/1992 | Bolich et al. | 424/70 |
| 5,106,609 | 4/1992 | Bolich et al. | 424/70 |
| 5,166,276 | 11/1992 | Hayama et al. | 524/329.7 |

*Primary Examiner*—Jyothsan Venkat
*Attorney, Agent, or Firm*—Leonard W. Lewis; Tara M. Rosnell; Loretta J. Henderson

[57] ABSTRACT

Disclosed are hair care compositions containing a hair styling/conditioning copolymer solubilized or dispersed in a volatile silicone fluid, wherein the copolymer-volatile silicone fluid solution further comprises a nonvolatile plasticizer.

22 Claims, No Drawings

HAIR CARE COMPOSITIONS HAVING STYLING/CONDITIONING AGENT AND PLASTICIZER

This is a continuation of application Ser. No. 08/026,144, filed on Mar. 2, 1993, now abandoned, which is a continuation of application Ser. No. 07/671,578, filed on Mar. 19, 1991, now abandoned.

TECHNICAL FIELD

The present invention relates to hair care compositions having a hair styling/hair conditioning component, especially rinse-off hair conditioning compositions containing hair styling/hair conditioning agents.

BACKGROUND OF THE INVENTION

The desire to have hair retain a particular shape is widely held. Such style retention is generally accomplished by either of two routes: permanent chemical alteration or temporary alteration of hair style/shape. A temporary alteration is one which can be removed by water or by shampooing. Temporary style alteration has generally been accomplished by means of the application of a composition to dampened hair after shampooing and/or conditioning and prior to drying and/or styling. The materials used to provide setting benefits have generally been resins or gums and have been applied in the form of mousses, gels, lotions, or sprays. This approach presents several significant drawbacks to the user. It generally requires a separate step following shampooing and conditioning to apply the styling composition. In addition, since the style hold is provided by resin materials which set-up on the hair, the hair tends to feel sticky or stiff after application and it is difficult to restyle the hair without further application of the styling composition.

The desire to condition the hair is also widely held. Compositions which "condition" the hair generally improve manageability, appearance, or the feel of the hair, or a combination thereof, such as by reducing dry static, increasing the wet and/or dry combing ease of the hair, etc. Such conditioning products are well known. Some are "rinse-off" type products which are applied and eventually rinsed off the hair, typically subsequent to shampooing. Many of these conditioning products contain cationic conditioning agents such as cationic long chain amines and long chain quaternary ammonium compounds, such as disclosed, for example, in U.S. Pat. No. 3,155,591, Hilvert, issued Nov. 3, 1964 and U.S. Pat. No. 4,269,824, Villamarin, et al., issued May 26, 1981. Other hair conditioning materials that have been used, especially in recent years, are siloxanes (see, for example, U.S. Pat. No. 3,208,911, Oppliger, issued Sep. 28, 1965) and siloxane-containing polymers. U.S. Pat. No. 4,601,902, Fridd et al., issued Jul. 22, 1986, describes hair conditioning or shampoo/conditioner compositions which include a polydiorgano-siloxane having quaternary ammonium substituted groups attached to the silicon, and a polydiorganosiloxane having silicon-bonded substituents which are amino-substituted hydrocarbon groups. U.S. Pat. No. 4,654,161, Kollmeier et al., issued Mar. 31, 1987, describes a group of organopolysiloxanes containing betaine substituents. When used in hair care compositions, these compounds are said to provide good conditioning, compatibility with anionic components, hair substantivity, and low skin irritation. U.S. Pat. No. 4,563,347, Starch, issued Jan. 7, 1986, relates to hair conditioning compositions which include siloxane components containing substituents to provide attachment to hair. Japanese Published Application 56-129,300, Lion Corporation, published Oct. 9, 1981, relates to shampoo conditioner compositions which include an organopolysiloxane-oxyalkylene copolymer together with an acrylic resin. U.S. Pat. No. 4,479,893, Hirota et al., issued Oct. 30, 1984, describes shampoo conditioner compositions containing a phosphate ester surfactant and a silicone derivative (e.g., polyether- or alcohol-modified siloxanes). Polyether-modified polysiloxanes are also disclosed for use in shampoos in U.S. Pat. No. 3,957,970, Korkis, issued May 18, 1976. U.S. Pat. No. 4,185,087, Morlino, issued Jan. 22, 1980, describes quaternary nitrogen derivatives of trialkylamino hydroxy organosilicon compounds which are said to have superior hair conditioning properties.

In practice, many consumers of hair care products first shampoo and condition their hair, and then apply a styling composition in order to aid in shape retention. This procedure has several disadvantages. It requires the inconvenience of separate application of the styling compositions. Also, the application of the conventional styling composition subsequent to conditioning can substantially counteract the benefits of the hair conditioner by giving the hair a more sticky or stiff feel.

Siloxane-derived materials have also been used in hair styling compositions. Japanese Published Application 56-092,811, Lion Corporation, published Dec. 27, 1979, describes hair setting compositions which comprise an amphoteric acrylic resin, a polyoxyalkylene-denatured organopolysiloxane, and polyethylene glycol. U.S. Pat. No. 4,744,978, Homan et al., issued May 17, 1988, describes hair styling compositions (such as hair sprays) which include the combination of a carboxyfunctional polydimethyl-siloxane and a cationic organic polymer containing amine or ammonium groups. Hair styling compositions which include polydi-organosiloxanes and a cationic organic polymer are taught in U.S. Pat. No. 4,733,677, Gee et al., issued Mar. 29, 1988, and U.S. Pat. No. 4,724,851, Cornwall et al., issued Feb. 16, 1988. Finally, European Patent Application 117,360, Cantrell et al., published Sep. 5, 1984, discloses compositions, containing a siloxane polymer having at least one nitrogen-hydrogen bond, a surfactant, and a solubilized titanate, zirconate or germanate, which act as both a conditioner and a hair styling aid.

More recently, it has been discovered that hair care compositions comprising certain silicone macromer-containing copolymers provide excellent hair style retention benefits, together with hair conditioning. The compositions may be in any of the conventional forms including, but not limited to, hair rinses, tonics, mousses, lotions and gels. The compositions provide style hold while significantly reducing the stiff or sticky/tacky feel and negative dry hair properties, such as reduced combing ease, conventionally associated with hair styling resins. Further, hair to which the compositions of the present invention have been applied may be restyled several times without requiring reapplication of the compositions.

Silicone macromer-containing copolymers that can provide these styling/conditioning benefits are described in U.S. Ser. No. 07/505,760, filed Apr. 6, 1990 now abandoned, Torgerson, Bolich and Garbe, and U.S. Ser. No. 07/505,755, filed Apr. 6, 1990 now abandoned, Bolich and Torgerson. A variety of hair care compositions that can contain these silicone macromer-containing copolymers are described in U.S. Ser. No. 07/551,118, filed Jul. 16, 1990 now abandoned, Bolich, Norton, and Russell, U.S. Ser. No. 07/551,119 now abandoned, filed Jul. 16, 1990, Bolich, Norton, and Russell, and U.S. Ser. No. 07/551,120 now abandoned, filed Jul. 16, 1990, Bolich, Norton, and Russell.

Whereas these styling/conditioning copolymers can provide previously unknown combinations of hair styling and conditioning in a single material, and can be effectively delivered to the hair in hair care compositions to impart such benefits to the user, it remains desirable, and therefore an object of this invention, to provide hair care compositions which improve the style holding properties of these styling/conditioning copolymers while retaining the conditioning benefits that these copolymers can provide.

It is also an object of this invention to provide hair rinse compositions designed to be applied to the hair and subsequently be rinsed off that provide improved hair styling while maintaining good hair conditioning benefits.

It is also an object of this invention to provide hair care compositions containing hair styling/conditioning copolymers that have improved style hold ability, while retaining good hair conditioning properties.

It is yet a further object of this invention to provide hair care compositions containing hair styling/conditioning copolymers which can provide improved style achievability to the user, that is, to better enable the user to style hair to the shape and positioning desired.

It is still another object of this invention to provide improved resistance to humidity to hair styling/conditioning compositions containing the styling/conditioning copolymers refereed to above. It is desirable to improve style hold in high humidity conditions, since it is often inconvenient to reapply and style the hair when such conditions are incurred. Also, when styling agents that are affected by humidity the hair tends to become wet and sticky, and also tend to more easily become dirty or take on a "dirty" feel. Thus, improved resistance to humidity can both improve style hold performance and help the hair stay clean feeling longer under high humidity conditions.

These and other objects are obtained by the present invention which is described in the description which follows.

Unless otherwise indicated, all percentages are by weight of the composition and all ratios are weight ratios.

SUMMARY OF THE INVENTION

The present invention relates to hair care compositions having both hair styling and hair conditioniner properties, wherein the compositions contain a silicone macromer-containing hair styling/conditioning copolymer.

In these compositions, the hair styling/conditioning copolymer is delivered to the hair in solubilized form in a volatile solvent. Whereas a wide variety of solvents for the hair styling/ conditioning agent can be used, the preferred solvents are volatile silicone fluids, including both cyclic and linear silicones as well as volatile fluid siloxane derivatives. Volatile silicone fluids are preferred for use, especially in the case of compositions intended to be applied to the hair and then rinsed off with water, since they are immiscible in water, thereby facilitating deposition of the hair styling/conditioning agent onto the hair even subsequent to rinsing with water and preventing the active from leaching out into the water or other carrier fluid (e.g., lower alkanol) phase that may be utilized in the composition, they are substantially odor-free, they evaporate upon application without leaving behind a greasy or dirty-feeling residue, and they can provide a suitable vehicle for solubilizing or dispersing hair styling/conditioning agents of the type useful for application in hair rinse compositions. Whereas volatile silicone fluids can provide these benefits, it remains desirable to provide hair styling compositions having a hair styling/conditioning active which provides these benefits, but which provides improved styling performance as discussed above, while retaining the benefits of delivery via a volatile silicone fluid.

It has now been found that hair care compositions containing certain hair styling/conditioning copolymers delivered to the hair in a volatile silicone fluid solvent can be improved through the incorporation into the hair styling/conditioning copolymer-volatile silicone fluid solution of specific plasticizers that are both nonvolatile and miscible with the styling/conditioning copolymer-volatile silicone fluid solution.

More specifically, the present invention relates to a hair care composition comprising
(a) a hair styling/conditioning component comprising:
  (i) from about 0.1%1 to about 10.0% by weight of the composition, of a silicone macromer-containing hair styling/conditioning copolymer having a molecular weight (weight average) of from about 200,000 to about 1,000,000, said silicone macromer having a molecular weight (weight average) of about 1,000 to about 50,000 that is covalently bonded to a non-silicone organic polymer backbone or organic oligomeric unit portion of a polymeric backbone, said copolymer having a Tg of at least about −20° C.;
  (ii) from about 0.1% to about 99.7% of a solvent in which said copolymer is soluble or dispersible, said solvent being a volatile silicone fluid, said copolymer and solvent being provided in the form of a copolymer-solvent solution also containing element (a) (iii); and
  (iii) a nonvolatile plasticizer that is safe for topical application to the hair and skin of humans, wherein said plasticizer is miscible with said copolymer-solvent solution and said composition has a plasticizer:polymer weight ratio of from about 1:20 to about 1:1; and
(b) from 0% to about 99.7% of an additional carrier vehicle suitable for application to the hair.

DETAILED DESCRIPTION OF THE INVENTION

The essential as well as optional components of the present compositions are described below.

The compositions herein will contain a hair styling conditioning component comprising a silicone macromer-containing styling/conditioning copolymer, a volatile silicone fluid solvent for the copolymer, and a plasticizer.

Silicone Macromer-Containing Hair Styling/Conditioning Copolymer

The compositions hereof contain a water-soluble silicone macromer-containing hair styling/conditioning copolymer. The term "water-insoluble" as it applies to the styling/conditioning copolymers means that the copolymer exists as an insoluble precipitate or forms a cloudy or hazy solution in water at a level of 1%, by weight, at 25° C. Such copolymers should have a weight average molecular weight of from about 200,000 to about 1,000,000, preferably from about 300,000 to about 800,000, more preferably from about 400,000 to about 600,000 and preferably, with said silicone macromer having a molecular weight (weight average) of about 1,000 to about 50,000 that is covalently bonded to a non-silicone organic polymer backbone or organic oligomeric unit portion of a polymeric backbone, said copolymer having a Tg of at least about −20° C. As used herein, the abbreviation "Tg" refers to the glass transition temperature of the backbone, and the abbreviation "Tm" refers to the crystalline melting point of the backbone, if such a transition exists for a given polymer. "Organic oligomeric portions of a polymeric backbone" shall mean the organic backbone portion of block copolymers containing siloxane blocks and organic blocks having carbon atoms in the organic portion of the backbone.

Preferred polymers comprise a vinyl polymeric backbone having a Tg or a Tm above about −20° C. and, grafted to the backbone, a polydimethylsiloxane macromer having a weight average molecular weight of from about 1,000 to about 50,000, preferably from about 5,000 to about 40,000, most preferably about 20,000.

The polymer is such that when it is formulated into the finished hair care composition, when dried, the polymer phase separates into a discontinuous phase which includes the polydi-methylsiloxane macromer and a continuous phase which includes the backbone.

The phase-separating nature of the compositions of the present invention may be determined as follows. The polymer is cast as a solid film out of a good solvent (i.e., a solvent which dissolves both the backbone and the silicone). This film is then sectioned and examined by transmission electron micrography. Microphase separation is demonstrated by the observation of inclusions in the continuous phase. These inclusions should have the proper size to match the size of the silicone chain (typically a few hundred nm or less) and the proper density to match the amount of silicone present. This behavior is well documented in the literature for polymers with this structure (see, for example, S. D. Smith, Ph.D. Thesis, University of Virginia, 1987, and references cited therein).

A second method for determining phase-separating characteristics involves examining the enrichment of the concentration of silicone at the surface of a polymer film relative to the concentration in the bulk polymer. Since the silicone prefers the low energy air interface, it preferentially orients on the polymer surface. This produces a surface which is entirely covered by silicone even when the concentration of the silicone by weight in the whole polymer is low (2% to 20%). This is demonstrated experimentally by ESCA (electron spectroscopy for chemical analysis) of the dried film surface. Such an analysis shows a high level of silicone and a greatly reduced level of backbone polymer when the film surface is analyzed. (Surface here means the first few tens of Angstroms of film thickness.) By varying the angle of the interrogating beam the surface can be analyzed to varying depths.

The polymers useful in the hair care compositions of the present invention include all properly defined copolymers of silicone with a non-silicone adhesive polymer. To be useful, such copolymers should satisfy the following four criteria:

(1) when dried the copolymer phase-separates into a discontinuous phase which includes the silicone portion and a continuous phase which includes the non-silicone portion;

(2) the silicone portion, i.e., the silicone macromer, is covalently attached to the non-silicone portion;

(3) the molecular weight of the silicone portion is from about 1,000 to about 50,000; and (4) the copolymer must be soluble or dispersible in the volatile silicone fluid solvent and permit the copolymer to deposit on hair.

In addition to the graft copolymers described above, useful copolymers include block copolymers containing up to about 50% (preferably from about 10% to about 20%) by weight of one or more polydimethyl siloxane blocks and one or more non-silicone blocks (preferably acrylates or vinyls).

In general, the styling/conditioning copolymers utilized in the present invention comprise "C" monomers together with monomers selected from the group consisting of "A" monomers, "B" monomers, and mixtures thereof. These copolymers contain at least A or B monomers, together with C monomers, and preferred copolymers contain A, B and C monomers.

Examples of useful copolymers and how they are made are described in detail in U.S. Pat. No. 4,693,935, Mazurek, issued Sep. 15, 1987, and U.S. Pat. No. 4,728,571, Clemens et al., issued Mar. 1, 1988, both of which are incorporated herein by reference. These copolymers are comprised of monomers A, C and, optionally, B, which are defined as follows. A is at least one free radically polymerizable vinyl monomer or monomers. B, when used, comprises at least one reinforcing monomer copolymerizable with A and is selected from the group consisting of polar monomers and macromers having a Tg or a Tm above about −20° C. When used, B may be up to about 98%, preferably up to about 80%, more preferably up to about 20%, of the total monomers in the copolymer. Monomer C comprises from about 0.01% to about 50.0% and the total monomers in the copolymer.

Representative examples of A monomers are acrylic or meth-acrylic acid esters of $C_1$–$C_{18}$ alcohols, such as methanol, ethanol, 1-propanol, 2-propanol, 1-butanol, 2-methyl-1-propanol, 1-pentanol, 2-pentanol, 3-pentanol, 2-methyl-1-butanol, 1-methyl-1-butanol, 3-methyl-1-butanol, 1-methyl-1-pentanol, 2-methyl-1-pentanol, 3-methyl-1-pentanol, t-butanol, cyclohexanol, 2-ethyl-1-butanol, 3-heptanol, benzyl alcohol, 2-octanol, 6-methyl-1-heptanol, 2-ethyl-1-hexanol, 3,5-dimethyl-1-hexanol, 3,5,5-tri-methyl-1-hexanol, 1-decanol, 1-dodecanol, 1-hexadecanol, 1-octadecanol, and the like, the alcohols having from about 1–18 carbon atoms with the average number of carbon atoms being from about 4–12; styrene; vinyl acetate; vinyl chloride; vinylidene chloride; acrylonitrile; alpha-methylstyrene; t-butylstyrene; butadiene; cyclohexadiene; ethylene; propylene; vinyl toluene; and mixtures thereof. Preferred A monomers include n-butyl methacrylate, isobutyl methacrylate, 2-ethylhexyl methacrylate, methyl meth-acrylate, t-butylacrylate, t-butylmethacrylate, and mixtures thereof.

Representative examples of B monomers include acrylic acid, methacrylic acid, N,N-dimethylacrylamide, dimethylaminoethyl methacrylate, quaternized dimethylaminoethyl methacrylate, meth-acrylonitrile, polystyrene macromer, methacrylamide, maleic anhydride and its half esters, itaconic acid, acrylamide, acrylate alcohols, hydroxyethyl methacrylate, diallyldimethyl ammonium chloride, vinyl pyrrolidone, vinyl ethers (such as methyl vinyl ether), maleimides, acylactones, 2-ethyl-2-oxazoline, vinyl pyridine, vinyl imidazole, other polar vinyl heterocyclics, styrene sulfonate, and mixtures thereof. Preferred B monomers include acrylic acid, N,N-dimethylacrylamide, dimethylaminoethyl methacrylate, quaternized dimethylaminoethyl methacrylate, vinyl pyrrolidone, and mixtures thereof.

The C monomer is the element of the styling/conditioning copolymers that constitutes the silicone-containing macromer portion of the copolymer. The C monomer has the general formula:

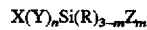

wherein X is a vinyl group copolymerizable with the A and B monomers; Y is a divalent linking group; R is a hydrogen, lower alkyl, aryl or alkoxy; Z is a monovalent siloxane polymeric moiety having a number average molecular weight of at least about 500, is essentially unreactive under copolymerization conditions and is pendant from the vinyl polymeric backbone, described above; n is 0 or 1; and m is an integer from 1 to 3. C has a weight average molecular weight of from about 1,000 to about 50,000, preferably from about 5,000 to about 40,000, most preferably from about 10,000 to about 20,000. Preferably, the C monomer has a formula selected from the following group (including mixtures thereof):

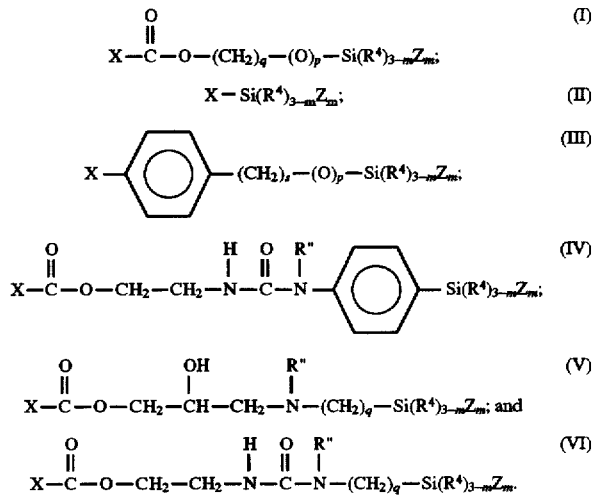

In those structures, m is 1, 2 or 3 (preferably m=1); p is 0 or 1; R" is alkyl or hydrogen; q is an integer from 2 to 6; s is an integer from 0 to 2; X is

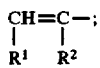

$R^1$ is hydrogen or —COOH (preferably $R^1$ is hydrogen); $R^2$ is hydrogen, methyl or —CH$_2$COOH (preferably $R^2$ is methyl); Z is

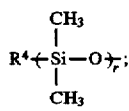

$R^4$ is alkyl, alkoxy, allkylamino, aryl, or hydroxyl (preferably $R^4$ is alkyl); and r is an integer from about 5 to about 700 (preferably r is about 250). Particularly preferred for C monomers of Formula I is when p=0 and q=3.

Highly preferred examples of such materials are the graft silicone-containing copolymers as described in the following patent applications: Ser. No. 07/505,760, Torgerson, Bolich and Garbe, filed Apr. 6, 1990 now abandoned; and Ser. No 07/505,755 now abandoned, Bolich and Torgerson, filed Apr. 6, 1990; both of which are incorporated by reference herein.

The preferred polymers useful in the present invention generally comprise from 0% to about 98% (preferably from about 5% to about 98%, more preferably from about 50% to about 90%) of monomer A, from 0% to about 98% (preferably from about 7.5% to about 80%) of monomer B, and from about 0.1% to about 50% (preferably from about 0.5% to about 40%, most preferably from about 2% to about 25%) of monomer C. The combination of the A and B monomers preferably comprises from about 50.0% to about 99.9% (more preferably about 60% to about 99%, most preferably from about 75% to about 95%) of the polymer. The composition of any particular copolymer will help determine its formulational properties. For example, polymers which are soluble in an aqueous formulation preferably have the composition: from 0% to about 70% (preferably from about 5% to about 70%) monomer A, from about 30% to about 98% (preferably from about 3% to about 80%) monomer B, and from about 1% to about 40% monomer C. Polymers which are dispersible have the preferred composition: from 0% to about 70% (more preferably from about 5% to about 70%) monomer A, from about 20% to about 80% (more preferably from about 20% to about 60%) monomer B, and from about 1% to about 40% monomer C.

Particularly preferred polymers for use in the present invention include the following (the weight percents below refer to the amount of reactants added in the polymerization reaction, not necessarily the amount in the finished polymer):

acrylic acid/n-butylmethacrylate/polydimethylsiloxane (PDMS) macromer-20,000 molecular weight (e.g., 10/70/20 w/w/w) (I)

N,N-dimethylacrylamide/isobutyl methacrylate/PDMS macromer-20,000 molecular weight (e.g., 20/60/20 w/w/w) (II)

dimethylaminoethyl methacrylate/isobutyl methacrylate/ 2-ethylhexyl-methacrylate/ PDMS macromer-20,000 molecular weight (e.g., 25/40/15/20 w/w/w/w) (III)

t-butylacrylate/t-butylmethacrylate/PDMS macromer-10,000 molecular weight (e.g., 56/24/20 w/w/w) (IV)

t-butylacrylate/PDMS macromer-10,000 molecular weight (e.g., 80/20 w/w) (V)

t-butylacrylate/N,N-dimethylacrylamide/PDMS macromer-10,000 molecular weight (e.g., 70/10/20 w/w/w) (VI)

t-butylacrylate/acrylic acid/PDMS macromer-10,000 molecular weight (e.g., 75/5/20 w/w/w) (VII).

The particle size of the copolymer material of the present compositions may have some effect on performance in product. This, of course, will vary from copolymer to copolymer and from product to product.

The compositions hereof will comprise from about 0.1% to about 10%, by weight of the composition, preferably from about 0.5% to about 8%, of the styling/conditioning copolymer.

Volatile Silicone Solvent

The copolymers are combined with a volatile solvent for the copolymer prior to combination with the carrier vehicle system.

The volatile solvents for use in this invention are silicone fluids. The styling/conditioning copolymer and volatile silicone fluid combination must be chosen such that the copolymer is compatible with, i.e., soluble or dispersible in, the solvent. The term "solution" shall be used to mean copolymer-volatile combinations wherein the copolymer is dissolved as well as when it is dispersed in the solvent.

The volatile solvents used hereof include any, volatile silicone fluid which is capable of dissolving or dispersing styling/conditioning copolymers. As used herein with respect to silicone fluids, "volatile" means that the fluid has a measurable and practicably significant (for hair care product formulation) vapor pressure at atmospheric pressure and 25° C. It will be understood by those skilled in the art that this means that the solvent will evaporate within a reasonable time after use such that the styling/conditioning copolymer dries to form the film which styles the hair.

The volatile silicones useful herein include cyclic silicone fluids such as cyclic polydimethylsiloxane. The number of silicon atoms in the cyclic silicones is preferably from about 3 to about 7, more preferably 4 or 5.

The general formula for such silicones is

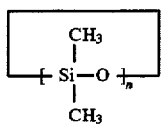

wherein n=3–7. The cyclic polydimethylsiloxanes generally have a viscosity at one atmospheric pressure, 25° C. of less than about 10 centipoise.

Volatile silicone fluids are widely known in the art. A description of volatile silicones is found in Todd and Byers. "Volatile Silicone Fluids for Cosmetics," *Cosmetics and Toiletries*, Vol. 91, January 1976, pp. 27–32, incorporated herein by reference.

Linear silicone fluids can also be used. Nonvolatile linear silicone fluids will generally have a viscosity of less than about 5 centipoise at one atmosphere, 25° C. Volatile linear silicones are exemplified by polydimethylsiloxanes having from about 3 to 9 silicone atoms, and having the general formula

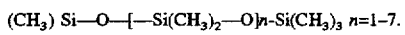

$(CH_3)Si-O-[-Si(CH_3)_2-O]_n-Si(CH_3)_3$ $n=1-7$.

Silicones of the above type, both cyclic and linear, are available from Dow Corning Corporation, Dow Corning 344, 345 and 200 fluids; Union Carbide, Silicone 7202 and Silicone 7158; and Stauffer Chemical, SWS-03314.

Other volatile silicone fluids include such siloxane derivatives as pentamethyldisiloxane, phenyl pentamethyl disiloxane, methoxypropyl heptamethyl cyclotetrasiloxane, chloropropyl pentamethyl disiloxane, hydroxypropyl pentamethyl disiloxane, octamethyl cyclotetrasiloxane, and decamethyl cyclopentasiloxane.

Whether particular copolymers will be soluble or dispersible in particular volatile silicone fluids will depend upon the nature of the chosen materials. As will be readily apparent to those skilled in the art, this will depend upon such factors as molecular weight of the styling/conditioning copolymer and the relative polarities of the copolymer and the volatile silicone fluid.

Preferred volatile solvents are cyclic and linear polydimethyl siloxanes, especially cyclic polydimethylsiloxanes.

The amount of solvent relative to the amount of copolymers in the styling/conditioning copolymer is not critical, except however the copolymer should be in solubilized or dispersed form as discussed above. Generally, the volatile solvent can comprise from about 0.1% to about 99.7%, by weight, of the composition, preferably from about 1% to about 15%, more preferably from about 2% to about 10%. The weight ratio of the volatile solvent:the styling/conditioning copolymer will preferably be about 1:1 or higher.

Plasticizer

The compositions also contain nonvolatile plasticizer as an essential ingredient. The plasticizer will be present in the compositions at a plasticizer:styling/conditioning copolymer weight ratio of about 1:20: to about 1:1, preferably from about 1:15 to about 1:2, more preferably from about 1:12 to about 1:2.5. As used herein, "nonvolatile" in regard to plasticizers means that the plasticizer exhibits essentially no vapor pressure at atmospheric pressure and 25° C. It is also highly preferred that the plasticizer not be odoriferous to the human nose, as any substantial plasticizer odor would affect perfumery of the product. The copolymer-volatile solvent solution should not suffer from substantial plasticizer weight loss while the volatile solvent is evaporating, since this would reduce plasticization of the copolymer during use. The plasticizers for use herein should generally have boiling points of about 250° C. or higher. Such plasticizers are nonvolatile for purposes hereof. Although it is not intended to be limited by theory, it is believed that the plasticizers can increase the flexibility and/or the flexibility of the film formed by the copolymer upon application of the composition to the hair and evaporation of the volatile silicone solvent. This can provide improved style hold, improved ability to achieve a desired style, and improved resistance to humidity. The plasticizers for use in the compositions must be safe for topical application to the hair and skin at the level present in the compositions.

The plasticizer should also be compatible with the hair styling/conditioning copolymer-volatile solvent solution. By "compatible" with respect to the plasticizer and the copolymer-volatile solvent solution, it is meant that the plasticizer does not adversely interact with the hair styling/conditioning copolymer, and must be miscible in said solution. In general, the nonvolatile plasticizers for use herein will be of relatively low water solubility. The solubility parameter, $\delta$, of these plasticizers will generally be between about 7 and about 10, preferably between about 8 and about 9 (units equal$(cal/cc)^{1/2}$). The solubility parameter is defined in the Polymer Handbook 3rd Ed. (John Wiley and Sons, New York), J. Brankrup and E. H. Immergut, Chapter VII, pp. 519–559, as the square root of the cohesive energy density and describes the attractive strength between molecules of the material. Solubility parameters may be determined by direct measurement, correlations with other physical properties, or indirect calculation as set forth by Immergut.

Plasticizers are well known in the art and are generally described in *Kirk-Othmer Encyclopedia of Chemical Technology*, second edition, Volume 15, pp. 720–789 (John Wiley & Sons, Inc. New York, 1968) under the topic heading "Plasticizers", and by J. Kern Sears and Joseph R. Darby in the text *The Technology of Plasticizers* (John Wiley & Sons, Inc., New York, 1982), both incorporated herein by reference. See especially in the Appendix of Sears/Darby Table A.9, at pages 983–1063 where a wide variety of plasticizers are disclosed.

The plasticizers for use herein include both cyclic and acyclic nonvolatile materials. Suitable categories of nonvolatile plasticizers include adipates, phthalates, isophthalates, azelates, stearates, citrates, trimellitates, silicone copolyols iso $C_{14}-C_{22}$ alcohols, methyl alkyl silicones, carbonates, sebacates, isobutgrates, oleates, phosphates, myristates, ricinoleates, pelargonates, valerates, oleates, camphor, and castor oil.

Examples of adipate plasticizers include adipic acid derivatives such as diisobutyl adipate, bis(2-ethylhexyl) adipate, diisodecyl adipate, bis(2-butoxyethyl) adipate, and di-n-hexyl adipate.

Examples of phthalate plasticizers include phthalic acid derivatives such as dibutyl phthalate, butyl octyl phthalate, di-n-octyl phthalate, diisooctyl phthalate, bis(2-ethylhexyl) phthalate, n-octyl n-decyl phthalate, di-n-hexyl phthalate, isooctyl isodecyl phthalate, diisodecyl phthalate, ditridecyl phthalate, butyl cyclohexyl phthalate, diisoctyl benzyl phthalate, butyl benzyl phthalate, dicyclohexyl phthalate, diphenyl phthalate, isodecyl benzyl phthalate, and bis(2-butoxyethyl) phthalate.

Isophthalate plasticizers include bis(2-ethylhexyl) isophthalate, and diisooctyl benzyl phthalate.

Examples of azelate plasticizers include azelaic acid derivatives such as di(2-ethylhexyl) azelate, and bis(2-ethylhexyl) azelate.

Examples of stearate plasticizers include stearic acid derivatives such as n-butyl stearate, butyl acetoxystearate, and butoxyethyl stearate.

Examples of citrate plasticizers include citric acid derivatives such as acetyl tri-n-butyl citrate, tri-n-butyl citrate, and acetal tri-2-ethyl hexyl citrate.

Examples of trimellitate plasticizers include tri-(2-ethylhexyl) trimellitate, and triisooctyl trimellitate.

Other examples of plasticizers include dibutyl carbonate, butyl oleate, n-butyl, butyrate, isobutyl butyrate, isopropyl butyrate, dibutyl carbonate, ethyl palmitate, isooctyl palmitate, methyl ricinoleate, butyl ricinoleate, diisooctyl sebacate, triisobutyl phosphate, isodecy pelargonate, ethyl valerate, isocetyl alcohol, octododecanol, isopropyl myristate, isostearyl alcohol and methyl alkyl silicones having $C_2$–$C_{20}$ alkyl and from 1 to about 500 siloxane monomer units.

Silicone copolyols that can be used as plasticizers include polyalkylene oxide-modified polydimethylsiloxane of the formula:

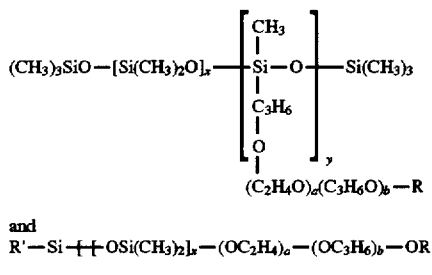

and
R'—Si ++OSi(CH₃)₂]ₓ—(OC₂H₄)ₐ—(OC₃H₆)ᵦ—OR"]₃ wherein R is hydrogen, an alkyl group having from 1 to about 12 carbon atoms, an alkoxy group having from 1 to about 6 carbon atoms or a hydroxyl group; R' and R" are alkyl groups having from 1 to about 12 carbon atoms; x is an integer of from 1 to 100, preferably from 20 to 30; y is an integer of 1 to 20, preferably from 2 to 10; and a and b are integers of from 0 to 50, preferably from 20 to 30.

Polydimethylsiloxane copolyols are also disclosed in the following patent documents, all incorporated by reference herein: U.S. Pat. No. 4,122,029, Geen, et al., issued Oct. 24, 1978; U.S. Pat. No. 4,265,878, Keil, issued May 5, 1981; and U.S. Pat No. 4,421,769, Dixon, et al., issued Dec. 20, 1983. Such dimethicone copolyol materials are also disclosed, in hair compositions, in British Patent Application 2,066,659, Abe, published Jul. 15, 1981 (incorporated by reference herein) and Canadian Patent 727,588, Kuehns, issued Feb. 8, 1966 (incorporated by reference herein). Commerically available dimethicone polydimethyl-siloxane copolyols which can be used herein, include Silwet Surface Active Copolymers (manufactured by the Union Carbide Corporation); and Dow Corning Silicone Surfactants (manufactured by the Dow Corning Corporation).

Carrier System

The compositions optionally comprise, a carrier vehicle suitable for application to the hair in addition to the volatile silicone fluid. A wide variety of carrier vehicles may be utilized. In general, the compositions will comprise from about 0% to about 99.7% of the carrier vehicle, typically from about 0.5% to about 98%, preferably from about 65% to about 98%, of the carrier vehicle.

As used herein, the phrase "suitable for application to hair" means that the carrier system does not damage or negatively affect the aesthetics of hair or cause irritation to skin. Choice of appropriate carrier will also depend on the particular copolymer to be used, and whether the product formulated is meant to be left on hair (e.g., mousse, tonic) or rinsed off (e.g., hair rinse) after use.

The carrier vehicles used herein include solvents as well as other carrier or vehicle components used in the hair care composition. They also include multi-component systems. Preferred carrier vehicle solvents for use in the present invention include water, lower alcohols ($C_1$–$C_4$ alcohols, preferably $C_2$–$C_4$ alcohols such as ethanol, isopropanol), and mixtures of water and lower alcohols. Preferred solvents include water, ethanol, and mixtures thereof.

The carrier vehicle may include thickening materials to increase viscosity of the composition. This is especially desirable for compositions that are rinsed off after use such as shampoos, hair rinses, as well as products intended to be left on the hair throughout the day such as gels, creams, mousses, etc. One type of thickening materials that can be used are gel vehicle materials. In essence, these materials form a gel network, in combination with the solvent. The gel vehicle comprises two essential components: a lipid vehicle material and a cationic surfactant vehicle material. A variety of suitable cationic surfactant materials are described in detail below. Gel-type vehicles are generally described in the following documents, all incorporated by reference herein: Barry, "The Self Bodying Action of the Mixed Emulsifier Sodium Dodecyl Sulfate/Cetyl Alcohol", 28 *J. of Colloid and Interface Science* 82–91 (1968); Barry, et al., "The Self-Bodying Action of Alkyltrimethylammonium Bromides/Cetostearyl Alcohol Mixed Emulsifiers; Influence of Quaternary Chain Length", 35 *J. of Colloid and Interface Science* 689–708 (1971); and Barry, et al., "Rheology of Systems Containing Cetomacrogol 1000-Cetostearyl Alcohol, I. Self Bodying Action", 38 *J. of Colloid and Interface Science* 616–625 (1972).

The carrier vehicles may incorporate one or more lipid vehicle materials which are essentially water-insoluble, and contain hydrophobic and hydrophilic moieties. Lipid vehicle materials include naturally or synthetically-derived acids, acid derivatives, alcohols, esters, ethers, ketones, and amides with carbon chains of from about 12 to about 22, preferably from about 16 to about 18, carbon atoms in length. Fatty alcohols and fatty esters are preferred; fatty alcohols are particularly preferred.

Lipid vehicle materials among those useful herein are disclosed in *Bailey's Industrial Oil and Fat Products*, (3rd edition, D. Swern, ed., 1979), incorporated by reference herein. Fatty alcohols included among those useful herein are disclosed in the following documents, all incorporated by reference herein: U.S. Pat. No. 3,155,591, Hilfer, issued Nov. 3, 1964; U.S. Pat. No. 4,165,369, Watanabe, et al., issued Aug. 21, 1979; U.S. Pat. No. 4,269,824, Villamarin, et al., issued May 26, 1981; British Specification 1,532,585, published Nov. 15, 1978; and Fukushima, et al., "The Effect of Cetostearyl Alcohol in Cosmetic Emulsions", 98 *Cosmetics & Toiletries* 89–112 (1983). Fatty esters included among those useful herein are disclosed in U.S. Pat. No. 3,341,465, Kaufman, et al., issued Sep. 12, 1976 (incorporated by reference herein). If included in the compositions of the present invention, the lipid vehicle material is generally present at from about 0.1% to about 10.0% of the composition; the cationic surfactant vehicle material is generally present at from about 0.5% to about 5.0% of the composition.

Preferred esters for use herein include cetyl palmitate and glycerylmonostearate. Cetyl alcohol and stearyl alcohol are preferred alcohols. A particularly preferred lipid vehicle material is comprised of a mixture of cetyl alcohol and stearyl alcohol containing from about 55% to about 65% (by weight of mixture) of cetyl stearyl alcohol.

Preferred carrier vehicles for use in the compositions of the present invention include hydrophobically-modified nonionic water soluble polymer (preferably the nonionic water-soluble polymer is hydroxyethyl cellulose) as a thickening material, in combination with certain surfactants and solvents, as described in detail in the following patent applications, each of which is incorporated herein by reference: U.S. Ser. Nos. 07/551,118, 07/551,119, and 07/551,120, all filed Jul. 16, 1990, by Bolich, Norton, and Russell.

In these carrier systems, a hydrophobically modified nonionic water-soluble polymer is present as a thickener. By "hydrophobically modified nonionic water-soluble polymer" is meant a nonionic water-soluble polymer which has been modified by the substitution with a sufficient amount of hydrophobic groups to make the polymer less soluble in water. By "water-soluble" what is meant is the polymer or salt, thereof, constituting the polymer backbone of the thickener should be sufficiently soluble such that it forms a substantially clear solution when dissolved in water at a level of 1%, by weight of the solution, at 25° C. Hence, the polymer backbone of the primary thickener can be essentially any water-soluble polymer. The hydrophobic groups can be $C_8$ to $C_{22}$ alkyl, aryl alkyl, alkyl aryl groups and mixtures thereof. The degree of hydrophobic substitution on the polymer backbone should be from about 0.10% to about 1.0%, depending on the particular polymer backbone. More generally, the ratio of hydrophilic portion to hydrophobic portion of the polymer is from about 10:1 to about 1000:1.

It is important that this thickener be well-hydrated and dispersed in the compositions of the present invention.

A number of existing patents disclose nonionic polymer materials which meet the above requirements and which are useful in the present invention. U.S. Pat. No. 4,496,708, Dehm et al., issued Jan. 29, 1985, teaches water-soluble polyurethanes having hydrophilic polyether backbones and pendant monovalent hydrophobic groups to result in a hydrophilic/lipophilic balance of between about 14 and about 19.5. U.S. Pat. No. 4,426,485, Hoy et al., issued Jan. 17, 1984, discloses a water-soluble thermo-plastic organic polymer having segments of bunched monovalent hydrophobic groups. U.S. Pat. No. 4,415,701, Bauer, issued Nov. 15, 1983, discloses copolymers containing a monoepoxide and a dioxolane.

The most preferred of these thickener materials are disclosed in U.S. Pat. No. 4,228,277, Landoll, issued Oct. 14, 1980, which is incorporated herein by reference. The materials disclosed therein are thickeners comprising a nonionic long chain alkylated cellulose ether.

The cellulose ethers have a sufficient degree of nonionic substitution selected From the group consisting of methyl, hydroxyethyl and hydroxypropyl to cause them to be water-soluble. The cellulose ethers are further substituted with a hydrocarbon radical having about 10 to 24 carbon atoms in an amount between about 0.2 weight percent and the amount which renders said cellulose ether less than about 0.2%, by weight, preferably less than 1%, soluble in water. The cellulose ether to be modified is preferably one of low to medium molecular weight, i.e., less than about 800,000 and preferably between about 20,000 and 700,000 (about 75 to 2500 D.P.).

The Landoll patent teaches that any nonionic water-soluble cellulose ether can be employed as the cellulose ether substrate. Thus, e.g., hydroxyethyl cellulose, hydroxypropyl cellulose, methyl cellulose, hydroxypropyl methyl cellulose, ethyl hydroxyethyl cellulose, and methyl hydroxyethyl cellulose can all be modified. The amount of nonionic substituent such as methyl, hydroxyethyl or hydroxypropyl is taught not to be critical so long as there is an amount sufficient to assure that the ether is water-soluble.

The preferred cellulose ether substrate is hydroxyethyl cellulose (HEC) of about 50,000 to 700,000 molecular weight. Hydroxyethyl cellulose of this molecular weight level is the most hydrophilic of the materials contemplated. It can thus be modified to a greater extent than can other water-soluble cellulose ether substrates before insolubility is achieved. Accordingly, control of the modification process and control of the properties of the modified product can be more precise with this substrate. Hydrophilicity of the most commonly used nonionic cellulose ethers varies in the general direction: hydroxyethyl→hydroxypropyl→hydroxypropyl methyl→methyl.

The long chain alkyl modifier can be attached to the cellulose ether substrate vial an ether, ester or urethane linkage. The ether linkage is preferred.

Although the materials taught in Landoll are referred to as being "long chain alkyl group modified", it will be recognized that except in the case where modification is effected with an alkyl halide, the modifier is not a simple long chain alkyl group. The group is actually an alphahydroxyalkyl radical in the case of an epoxide, a urethane radical in the case of an isocyanate, or an acyl radical in the case of an acid or acyl chloride. Nonetheless, the terminology "long chain alkyl group" is used since the size and effect of the hydrocarbon portion of the modifying molecule completely obscure any noticeable effect from the connecting group. Properties are not significantly different from those of the product modified with the simple long chain alkyl group.

One commercially available material which meets these requirements is NATROSOL PLUS Grade 330, a hydrophobically modified hydroxyethylcellulose available from Aqualon Company, Wilmington, Del. This material has a $C_{16}$ alkyl substitution of from about 0.4% to about 0.8% by weight. The hydroxyethyl molar substitution for this material is from about 3.0 to about 3.7. The average molecular weight for the water-soluble cellulose prior to modification is approximately 300,000. Another material of this type has a $C_{16}$ alkyl substitution of from about 0.40% to about 0.95%, by weight. The hydroxyethyl molar substitution for this material is from about 2.3 to about 3.3, and may be as high as about 3.7. The average molecular weight for the water soluble cellulose prior to modification is approximately 700,000.

Such thickener components in these types of carrier vehicles is generally present in the compositions at from about 0.1% to about 10.0%, preferably from about 0.2% to about 5.0%.

The carrier vehicles containing hydrophobically modified cellulose as thickener material further comprise, as a second component, secondary thickener selected from water-insoluble surfactants having a molecular weight of less than about 20,000, water-soluble surfactants having a molecular weight of less than 20,000, or a water-soluble polymer having a molecular weight greater than about 20,000. It is preferred to utilize water-insoluble surfactants as the secondary thickener. In any case, the compositions containing the hydrophobically modified cellulose thickening materials in the carrier system preferably do not contain any more than about 1.0% of water-soluble surfactants, preferably no more than about 0.5%. By "water-insoluble surfactant" is meant surfactant materials which do not form clear isotropic solutions when dissolved in water at greater than 0.2 weight percent at 25° C. By "water-soluble polymer", in regard to this component, is meant that the material will form substantially a clear solution in water at a 1% concentration at 25° C. and the material will increase the viscosity of the water. By "water-soluble surfactant" is meant surfactant materials which form clear isotropic solutions when dissolved in water at 0.2 weight percent at 25° C.

Nonlimiting examples of surfactants which can be used in the vehicle systems of the compositions of the present invention can be selected from anionic, nonionic, cationic, zwitterionic and amphoteric surfactants. Preferred are cationic surfactants.

Synthetic anionic surfactants include alkyl and alkyl ether sulfates. These materials have the respective formulae ROSO3M and RO($C_2H_4O$)$_x$SO$_3$M, wherein R is alkyl or alkenyl of from about 10 to about 20 carbon atoms, x is 1 to 10, and M is a water-soluble cation such as ammonium, sodium, potassium and triethanolamine. The alkyl ether sulfates useful in the present invention are condensation products of ethylene oxide and monohydric alcohols having from about 10 to about 20 carbon atoms. Preferably, R has from about 14 to about 20 carbon atoms in both the alkyl and alkyl ether sulfates.

Specific examples of alkyl ether sulfates which can be used in the present invention are sodium tallow alkyl diethylene glycol ether sulfate; and sodium tallow alkyl sulfate.

Another suitable class of anionic surfactants are the salts of the organic, sulfuric acid reaction products of the general formula:

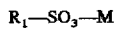
$R_1$—$SO_3$—M wherein $R_1$ is chosen from the group consisting of a straight or branched chain, saturated aliphatic hydrocarbon radical having from about 8 to about 24, preferably about 18 to about 22, carbon atoms; and M is a cation.

Additional examples of anionic synthetic surfactants which can be used in the present invention are the reaction products of fatty acids esterified with isethionic acid and neutralized with sodium hydroxide where, for example, the fatty acids are derived from tallow oil; sodium or potassium salts of fatty acid amides of methyl tauride in which the fatty acids, for example, are derived from tallow oil. Other anionic synthetic surfactants of this variety are set forth in U.S. Pat. Nos. 2,486,921; 2,486,922; and 2,396,278.

Still other anionic synthetic surfactants include the class designated as succinamates. This class includes such surface active agents as disodium N-octadecylsulfosuccinamate; tetrasodium N-(1,2-dicarboxyethyl)-N-octadecylsulfosuccinamate; dioctyl esters of sodium sulfosuccinic acid.

Other suitable an-ionic surfactants utilizable herein are olefin sulfonates having about 12 to about 24 carbon atoms. The term "olefin sulfonates" is used herein to mean compounds which can be produced by the sulfonation of α-olefins by means of uncomplexed sulfur trioxide, followed by neutralization of the acid reaction mixture in conditions such that any sultones which have been formed in the reaction are hydrolyzed to give the corresponding hydroxy-alkanesulfonates.

In addition to the true alkene sulfonates and a proportion of hydroxy-alkanesulfonates, the olefin sulfonates can contain minor amounts of other materials, such as alkene disulfonates depending upon the reaction conditions, proportion of reactants, the nature of the starting olefins and impurities in the olefin stock and side reactions during the sulfonation process.

Many additional nonsoap synthetic anionic surfactants are described in *McCutcheon's, Detergents and Emulsifiers,* 1984 *Annual,* published by Allured Publishing Corporation, which is incorporated herein by reference. Also U.S. Pat. No. 3,929,678, Laughlin et al., issued Dec. 30, 1975, discloses many other anionic as well as other surfactant types and is incorporated herein by reference.

Nonionic surfactants can be broadly defined as compounds containing a hydrophobic moiety and a nonionic hydrophilic moiety. Examples of the hydrophobic moiety can be alkyl, alkyl aromatic, dialkyl siloxane, polyoxyalkylene, and fluoro-substituted alkyls. Examples of hydrophilic moieties are polyoxyalkylenes, phosphine oxides, sulfoxides, amine oxides, and amides. Examples of preferred classes of nonionic surfactants are:

1. The polyethylene oxide condensates of alkyl phenols, e.g., the condensation products of alkyl phenols having an alkyl group containing from about 6 to about 12 carbon atoms in either a straight chain or branched chain configuration, with ethylene oxide, the said ethylene oxide being present in amounts equal to from about 2 to about 6 moles of ethylene oxide per mole of alkyl phenol. The alkyl substituent in such compounds may be derived from polymerized propylene, diisobutylene, octane, or nonane, for example.

2. Those derived from the condensation of ethylene oxide with the product resulting from the reaction of propylene oxide and ethylene diamine products which may be varied in composition depending upon the balance between the hydrophobic and hydrophilic elements which is desired. For example, compounds containing from about 10% to about 40% polyoxyethylene by weight and having a molecular weight of from about 500 to about 4,000 resulting from the reaction of ethylene oxide groups with a hydrophobic base constituted of the reaction product of ethylene diamine and excess propylene oxide, said base having a molecular weight of the order of about 2,500 to about 10,000, are satisfactory.

3. The condensation product of aliphatic alcohols having from about 8 to about 20 carbon atoms, in either straight chain or branched chain configuration, with ethylene oxide, e.g., a tallow alcohol ethylene oxide condensate having from about 2 to about 10 moles of ethylene oxide per mole of tallow alcohol, the tallow alcohol fraction having from about 16 to about 18 carbon atoms.

4. Long chain tertiary amine oxides corresponding to the following general formula:

$R_1R_2R_3N{\rightarrow}O$ wherein $R_1$ contains an alkyl, alkenyl or monohydroxy alkyl radical of from about 12 to about 22 carbon atoms, from 0 to about 10 ethylene oxide moieties, and from 0 to about 1 glyceryl moiety, and $R_2$ and $R_3$ contain from about 1 to about 3 carbon atoms and from 0 to about 1 hydroxy group, e.g., methyl, ethyl, propyl, hydroxyethyl, or hydroxypropyl radicals. The arrow in the formula is a conventional representation of a semipolar bond. Examples of amine oxides suitable for use in this invention include dimethyloctadecylamine oxide, oleyldi(methyl) amine oxide, dimethylhexadecylamine oxide, behenyldimethylamine oxide.

5. Long chain tertiary phosphine oxides corresponding to the following general formula:

wherein R contains an alkyl, alkenyl or monohydroxyalkyl radical ranging from about 12 to about 22 carbon atoms in chain length, from 0 to about 10 ethylene oxide moieties and from 0 to about 1 glyceryl moiety and R' and R" are each alkyl or monohydroxyalkyl groups containing from about 1 to about 3 carbon atoms. The arrow in the formula is a conventional representation of a semipolar bond.

6. Long chain dialkyl sulfoxides containing one short chain alkyl or hydroxy alkyl radical of from about 1 to about 3 carbon atoms (usually methyl) and one long hydrophobic chain which include alkyl, alkenyl, hydroxy alkyl, or keto alkyl radicals containing from about 12 to about 20 carbon atoms, from 0 to about 10 ethylene oxide moieties and from 0 to about 1 glyceryl moiety.

7. Silicone copolyols such as those previously described.

8. Amide surfactants which include the ammonia, monoethanol, diethanol, and other alkanol amides of fatty acids having an acyl moiety of from about 8 to about 22 carbon atoms and represented by the general formula:

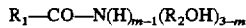

wherein $R_1$ is a saturated or unsaturated, aliphatic hydrocarbon radical having from 7 to 21, preferably from 11 to 17 carbon atoms; $R_2$ represents a $C_{1-4}$ alkalene group; and m is 1, 2 or 3, preferably 1. Specific examples of said amides are mono-ethanol coconut fatty acids amide and diethanol dodecyl fatty acid amide. These acyl moieties may be derived from naturally occurring glycerides, e.g., coconut oil, palm oil, soybean oil and tallow, but can be derived synthetically, e.g., by the oxidation of petroleum, or by hydrogenation of carbon monoxide by the Fischer-Tropsch process. The monoethanol amides and diethanolamides of $C_{18-22}$ fatty acids are preferred.

Cationic surfactants useful in carrier systems of the compositions of the present invention, including the gel vehicle systems as well as hydrophobically modified cellulose systems, contain amino or quaternary ammonium hydrophilic moieties which are positively charged when dissolved in the aqueous composition of the present invention. Cationic surfactants among those useful herein are disclosed in the following documents, all incorporated by reference herein: M.C. Publishing Co., *McCutcheon's. Detergents & Emulsifiers*, (North American Edition 1979); Schwartz, et al., *Surface Active Agents, Their Chemistry and Technology*, New York: Interscience Publishers, 1949; U.S. Pat. No. 3,155,591, Hilfer, issued Nov. 3, 1964; U.S. Pat. No. 3,929,678, Laughlin, et al., issued Dec. 30, 1975; U.S. Pat. No. 3,959,461, Bailey, et al., issued May 25, 1976; and U.S. Pat. No. 4,387,090, Bolich, Jr., issued Jun. 7, 1983.

Among the quaternary ammonium-containing cationic surfactant materials useful herein are water-insoluble surfactants of the general formula:

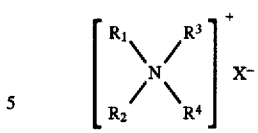

wherein $R_1$–$R_4$ can independently be selected from an aliphatic group of from about 1 to about 22 carbon atoms, $C_1$–$C_3$ alkyl, hydroxyalkyl, polyalkoxy or an aromatic, aryl or alkylaryl group having from about 12 to about 22 carbon atoms; and X is an anion selected from halogen, acetate, phosphate, nitrate and alkyl-sulfate radicals. The aliphatic groups may contain, in addition to carbon and hydrogen atoms, ether linkages, and other groups such as amino groups.

Other quaternary ammonium salts useful herein have the formula:

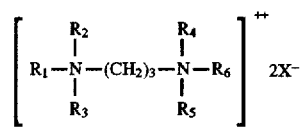

wherein $R_1$ is an aliphatic group having from about 16 to about 22 carbon atoms, $R_2$, $R_3$, $R_4$, $R_5$, and $R_6$ are selected from hydrogen and alkyl having from about 1 to about 4 carbon atoms, and X is an ion selected from halogen, acetate, phosphate, nitrate and alkyl sulfate radicals. Such quaternary ammonium salts include tallow propane diammonium dichloride.

Preferred quaternary ammonium salts include dialkyldimethyl-ammonium chlorides, wherein the alkyl groups have from about 12 to about 22 carbon atoms and are derived from long-chain fatty acids, such as hydrogenated tallow fatty acid (tallow fatty acids yield quaternary compounds wherein $R_1$ and $R_2$ have predominately from 16 to 18 carbon atoms). Examples of quaternary ammonium salts useful in the present invention include ditallowdimethyl ammonium chloride, ditallowdimethyl ammonium methyl sulfate, dihexadecyl dimethyl ammonium chloride, di(hydrogenated tallow) dimethyl ammonium chloride, dioctadecyl dimethyl ammonium chloride, dieicosyl dimethyl ammonium chloride, didocosyl dimethyl ammonium chloride, di(hydrogenated tallow) dimethyl ammonium acetate, dihexadecyl dimethyl ammonium chloride, dihexadecyl dimethyl ammonium acetate, ditallow dipropyl ammonium phosphate, ditallow dimethyl ammonium nitrate, di(coconutalkyl) dimethyl ammonium chloride, and stearyl dimethyl benzyl ammonium chloride. Ditallow dimethyl ammonium chloride, dicetyl dimethyl ammonium chloride, stearyl dimethyl benzyl ammonium chloride are exemplary quaternary ammonium salts useful herein.

Particularly useful cationic surfactants for use as thickeners and conditioners in carrier vehicles containing the hydrophobically modified water soluble polymers described above are selected from quaternary ammonium surfactants having the formula, in salt form:

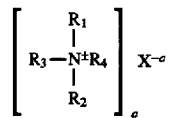 (I)

wherein X is a salt-forming anion, a is the ionic charge of X, the quaternary ammonium radicals $R_1$, $R_2$, $R_3$, and $R_4$ independently are $C_1$–$C_{22}$ alkyl, $C_{14}$–$C_{22}$ alkyl amido $C_2$–$C_6$ alkylene, or methyl benzyl, and from two to three of said quaternary ammonium radicals, preferably two, are $C_{14}$–$C_{22}$ alkyls or $C_{14}$–$C_{22}$ alkyl amido $C_2$–$C_6$alkylene (preferably $C_2$–$C_3$ alkylene), preferably $C_{16}$–$C_{22}$ alkyl, more preferably $C_{16}$–$C_{18}$ alkyl, or mixtures thereof, no more than two of said radicals are either $C_{14}$–$C_{22}$ alkyl amido $C_2$–$C_6$ alkylene or a combination of $C_{14}$–$C_{22}$ alkyl and $C_{14}$–$C_{22}$ alkyl amido $C_2$–$C_6$ alkylene, from one to three of said quaternary ammonium radicals, preferably two or three, are $C_1$–C6 alkyls, preferably $C_1$–$C_3$ alkyl, more preferably methyl, and no more than one of said radicals is methyl benzyl; or

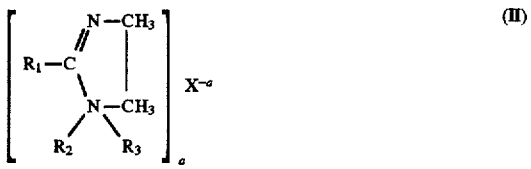

(II)

wherein X and a are as defined above, the radicals $R_1$, $R_2$, and $R_3$ independently are $C_1$–$C_{22}$ alkyl or methyl benzyl, preferably $C_1$–$C_{22}$ alkyl, and one or two of said radicals are $C_{14}$–$C_{22}$ alkyls, preferably $C_{16}$–$C_{22}$ alkyl, or $C_{14}$–$C_{22}$ alkylene (preferably $C_2$–$C_3$ alkylene), or a mixture thereof, one or two of said radicals are $C_1$–$C_6$ alkyl, preferably $C_1$–$C_3$ alkyl, more preferably methyl, zero or one of said radicals is methyl benzyl, wherein the quaternary ammonium surfactant component of the above description has a sufficient level unsaturation in the $C_{14}$–$C_{22}$ alkyl or $C_{14}$–$C_{22}$ alkyl amido $C_2$–$C_6$ alkylene radicals, or mixtures thereof, such that average iodine value of said component is at least about 15; or a mixture of Formula I and II surfactants.

Another specific category of cationic quaternary ammonium surfactants that can be advantageously incorporated into the present compositions in combination with the above-described essential unsaturated quaternary ammonium surfactants, are water-insoluble materials having the formula, in salt form,

(III)

wherein X is a salt-forming anion as previously described, a is the charge of the anion X, the radicals $R_1$, $R_2$, $R_3$, and $R_4$ independently are $C_1$–$C_6$ alkyl, $C_{20}$–$C_{22}$ alkyl, or methyl benzyl wherein one of said radicals is $C_{20}$–$C_{22}$ alkyl, preferably $C_{22}$, from two to three of said radicals are $C_1$–$C_6$ alkyl, preferably $C_1$–$C_3$, more preferably methyl, and zero or one of said radicals is methylbenzyl.

The long chain alkyl (i.e. the $C_{20}$–$C_{22}$ alkyl) can be either saturated or unsaturated.

A quaternary ammonium surfactant of Formula III particularly contemplated herein is: dimethyl behenyl benzyl ammonium salt (alternately referred to as behenalkonium salt), available from Witco Chemical Corp. (Memphis, Tenn., USA) as a chloride salt under the trade name Kemamine® BQ-280$_2$C. Another particularly contemplated Formula III material is dimethyl arachidyl benzyl ammonium salt.

The quaternary ammonium surfactant of Formula III is generally used at a level of from about 0.02% to about 10.0%, preferably from about 0.05% to about 3.0%, more preferably from about 0.05% to about 2.0%, by weight, of the composition.

Preferred combinations are compositions containing the surfactant of Formula III, especially in saturated form, in combination with the surfactants of Formulas I or II, or a mixture thereof, wherein the Formula I and II component comprises $C_{14}$–$C_{18}$ unsaturated alkyls, preferably at a weight ratio of (Formulas I and II):(Formula III) of about 1:1 to about 4:1.

A particularly useful combination of cationic surfactants that can be used comprises a mixture of di(unsaturated) C16–$C_{18}$ alkyl (preferably tallow) dimethyl ammonium salt (e.g. the chloride salt as commercially available from Sherex Chemicals under the tradename ADOGEN 470)) and dimethyl (saturated or unsaturated) behenyl and/or arachidyl, preferably saturated) methyl benzyl ammonium salt (e.g. the chloride salt, at a weight ratio of about 1:1 at about 4:1, more preferably about 1:1 to about 3:1.

These combinations of cationic surfactants can provide overall performance for hair styling/conditioning products, such as hair rinse products containing a styling/conditioning copolymer as described herein. Whereas the unsaturated quaternary ammonium surfactant thickener component, especially the dimethyl, di($C_{16}$–$C_{18}$) alkyl-substituted surfactants, can provide products with excellent rheology, hair conditioning, and style hold, style hold can be improved through the use of the long chain $C_{20}$–$C_{22}$ alkyl-substituted materials of Formula III while retaining the excellent rheology and conditioning benefits of the unsaturated thickener component.

Salts of primary, secondary and tertiary fatty amines are also preferred cationic surfactant materials for use herein. The alkyl groups of such amines preferably have from about 12 to about 22 carbon atoms, and may be substituted or unsubstituted. Secondary and tertiary amines are preferred, tertiary amines are particularly preferred. Such amines, useful herein, include stearamido propyl dimethyl amine, diethyl amino ethyl stearamide, dimethyl stearamine, dimethyl soyamine, soyamine, tri(decyl) amine, ethyl stearylamine, ethoxylated (2 moles E.O. ) stearylamine, dihydroxyethyl stearylamine, and arachidylbehenylamine. Suitable amine salts include the halogen, acetate, phosphate, nitrate, citrate, lactate and alkyl sulfate salts. Such salts include stearylamine hydrochloride, stearylamine formate, N-tallowpropane diamine dichloride and stearamidopropyl dimethylamine citrate. Cationic amine surfactants included among those useful in the present invention are disclosed in U.S. Pat. No. 4,275,055, Nachtigal, et al., issued Jun. 23, 1981, incorporated by reference herein.

Zwitterionic surfactants are exemplified by those which can be broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic water-solubilizing group, e.g., carboxy, sulfonate, sulfate, phosphate, or phosphonate. A general formula for these compounds is:

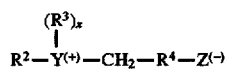

wherein $R^2$ contains an alkyl, alkenyl, or hydroxy alkyl radical of from about 8 to about 18carbon atoms, from 0 to about 10 ethylene oxide moieties and from 0 to about 1 glyceryl moiety; Y is selected from the group consisting of nitrogen, phosphorus, and sulfur atoms; $R^3$ is an alkyl or monohydroxyalkyl group containing about 1 to about 3 carbon atoms; X is 1 when Y is a sulfur atom, and 2 when Y is a nitrogen or phosphorus atom; $R^4$ is an alkylene or hydroxyalkylene of from about 1 to about 4 carbon atoms and Z is a radical selected from the group consisting of carboxylate, sulfonate, sulfate, phosphonate, and phosphate groups.

Other zwitterionics such as betaines are also useful in the present invention. Examples of betaines useful herein include the high alkyl betaines, such as stearyl dimethyl carboxymethyl betaine, behenyl dimethyl carboxymethyl betaine, stearyl bis-(2-hydroxypropyl) carboxymethyl betaine. The sulfobetaines may be represented by behenyl dimethyl sulfopropyl betaine, stearyl dimethyl sulfopropyl betaine, and the like; hydrogenated tallow dimethyl betaine; amidobetaines and amidosulfobetaines, wherein the RCONH(CH$_2$)$_3$ radical is attached to the nitrogen atom of the betaine are also useful in this invention.

Examples of amphoteric surfactants which can be used in the vehicle systems of the compositions of the present invention are those which are broadly described as derivatives of aliphatic secondary and tertiary amines in which the aliphatic radical can be straight or branched chain and wherein one of the aliphatic substituents contains from about 8 to about 18 carbon atoms and one contains an anionic water solubilizing group, e.g., carboxy, sulfonate, sulfate, phosphate, or phosphonate.

Examples of preferred water-insoluble surfactants for the hydrophobically modified cellulose carrier systems are stearamide DEA, cocamide MEA, dimethyl stearamine oxide, glyceryl monooleate, sucrose stearate, PEG-2 stearamine, Ceteth-2, a polyethylene glycol ether of cetyl alcohol of the formula CH$_3$-(CH$_2$)$_{14}$-CH$_2$-(OCH$_2$CH$_2$)$_n$-OH, where n has an average value of 2 (commerically available under the trade name Brij 56 from ICI Americas), glycerol stearate citrate, dihydrogenated tallow dimethyl ammonium chloride, Poloxamer 181, a polyoxyethylene, polyoxypropylene block polymer of the formula

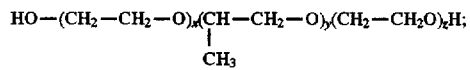

wherein on average x=3, y=30 and z=3 (commercially available from BASF Wyandotte under the trade name Pluronic L-61), hydrogenated tallow dimethyl betaine, and hydrogenated tallow amide DEA.

The water-insoluble surfactant is used with the hydrophobically modified polymer (primary thickener) at from about 0.02% to about 10.0%, preferably from about 0.05% to about 3.0%, most preferably from about 0.05% to about 2.0%, of the composition.

The water-soluble surfactant is used with the primary thickener at from about 0.02% to about 0.30%, preferably from about 0.05% to about 0.30%, most preferably from about 0.05% to about 0.20%, of the composition.

Examples of particularly preferred water-soluble surfactant materials for use in the hydrophobically modified polymer-based carrier vehicles are cetyl betaine, ammonium lauryl sulfate,ammonium laureth sulfate, and cetyl trimethyl ammonium chloride, and mixtures thereof.

The water-soluble polymeric thickening component is present in the compositions at from about 0.3% to about 5.0%, preferably from about 0.4% to about 3.0%.

Examples of water-soluble polymers which are desirably used as the additional thickening component to hydrophobically modified cellulose include hydroxyethyl cellulose, hydroxypropyl cellulose, hydroxypropyl methyl cellulose, polyethylene glycol, polyacrylamide, polyacrylic acid, polyvinyl alcohol, polyvinyl pyrrolidone K-120, dextrans, for example Dextran purified crude Grade 2P, available from D&O Chemicals, carboxymethylcellulose, plant exudates such as acacia, ghatti, and tragacanth, seaweed extracts such as sodium alginate, propylene glycol alginate, sodium carrageenan, and Ucare JR-polymer (a cationic modified hydroxyethyl cellulose available from Union Carbide). Preferred as the additional thickener are natural polysaccharide materials. Examples of such materials are guar gum, locust bean gum, and xanthan gum. Also preferred as the additional thickener is hydroxyethylcellulose having a molecular weight of about 700,000. These polymer materials preferably do not contain cellulase as this may interfere with obtaining optimum product viscosities.

The preferred solvents for use in carrier systems described above based upon hydrophobically modified cellulose with the specified additional thickeners are water or water-lower alkanol mixtures. The solvent is preferably present in these compositions at a level of from about 5% to about 99%, more preferably from about 65% to about 98% by weight of the composition.

Distributing Aid

An additional optional component in the carrier vehicles systems of the present invention is a material which acts as a distributing aid for the composition. Such a material helps to distribute the composition onto the hair avoiding localized deposition of the active component onto the hair or skin.

Examples of water soluble polymer materials which meet these requirements and hence, can act as distributing aids in the present compositions include xanthan gum; Dextran purified crude Grade 2P available from D&O chemicals; carboxymethyl celluloses; for example, CMC's 4H1F, 4M6F, 7HF, 7M8SF, 7LF, 9H4F, 9M8, 12M8P, 16M31, (all available from Aqualon); plant exudates such as acacia, ghatti and tragacanth; seaweed extracts such as sodium alginate, propylene glycol alginate, and sodium carrageenan; high molecular weight hydroxyethyl celluloses such as Natrosol 250H and Natrosol 250HHR (available from Aqualon); and pectin.

If a distributing aid is present in the cosmetic compositions of the present invention, it should be present at a level of from about 0.02% to about 2.5%, preferably from about 0.05% to about 1.0%, of the cosmetic composition. If the distributing aid is bifunctional, i.e., acting as both a thickener (as described above) and the distributing aid, it preferably is present at a level of from about 0.2% to about 5.0% of the composition.

A distributing aid is particularly useful in hair care compositions of the present invention especially rinse-off hair conditioners. The distributing aid helps to spread some hair conditioning components evenly over the hair.

Compositions having carrier vehicles based on the hydrophobically modified polymer primary thickener and additional secondary thickener as described above are preferably substantially free of fatty alcohol materials, such as stearyl-, cetyl-, myristyl-, behenyl-, lauryl-, and oleyl alcohol. By "substantially free of fatty alcohol materials" is meant that the compositions of the present invention comprise no more than about 1% of these fatty alcohol materials.

Other carrier vehicles, suitable for use with the present invention are, for example, those used in the formulation of tonics, mousses, gels and hair sprays. Tonics, gels and nonaerosol hair sprays utilize a solvent such as water or alcohol while mousses and aerosol hair sprays additionally utilize a propellant such as trichlorofluoromethane, dichlorodifluoromethane, dimethylether, propane, n-butane or isobutane. A tonic or hair spray product having a low viscosity may also require an emulsifying agent to keep the silicone copolymer homogeneously dispersed in solution. Examples of suitable emulsifying agents include nonionic, cationic, anionic surfactants, or mixtures thereof. If such an emulsifying agent is used, it is present at a level of from about 0.25% to about 7.5% of the composition. The level of propellant can be adjusted as desired but is generally from about 3% to about 30% of mousse compositions and from about 15% to about 50% of the aerosol hair spray compositions.

Optional Ingredients

The hair care compositions of the present invention may be formulated in a wide variety of product types, including mousses, gels, lotions, tonics, sprays, and conditioners. The additional components required to formulate such products vary with product type and can be routinely chosen by one skilled in the hair care product art. The following is a description of some of these additional components.

Surfactants are preferred optional ingredients in the compositions of the invention, particularly shampoo and hair rinse compositions. When present, the surfactant comprises from about 0.05% to about 50% of the composition. For a shampoo, the level is preferably from about 10% to about 30%, most preferably from about 12% to about 25%, of the composition. The hair rinses, the preferred level of surfactant is from about 0.2% to about 3%. Surfactants useful in compositions of the present invention include anionic, nonionic, cationic, zwitterionic and amphoteric surfactants. Suitable surfacatants are described in more detail above.

Cationic surfactants and nonvolatile silicone conditioning agents are particularly desirable for hair rinse products, to enhance hair conditioning provided by the hair styling/conditioning agent hereof.

Examples of antidandruff aids suitable for use with the vehicle systems of the present invention include zinc pyrithione, sulphur, and selenium sulfide. One example of a hair growth promoter suitable for use with the vehicle systems of the present invention is Minoxidil, (6-amino-1, 2-dihydro -1-hydroxy-2-imino-4-piperidino pyrimide) available from Upjohn. Hair oxidizing (bleaching) agents, such as hydrogen peroxide, perborate and persulfate salts, and hair reducing agents such as thioglycolates may also be used.

Examples of other hair conditioning materials suitable for use in the compositions of the present invention are silicone conditioning agents and volatile liquid hydrocarbons.

The volatile liquid hydrocarbons preferably have a boiling point in the range of about 99° C. to about 260° C. and have a solubility in water of less than about 0.1%. The hydrocarbons may be either straight or branched chain and may contain from about 10 to about 16, preferably from about 12 to about 16 carbon atoms. Examples of suitable hydrocarbons are decane, dodecane, tetradecane, tridecane and mixtures thereof.

Silicone conditioning agents include both volatile and non-volatile silicone fluids. Volatile silicones useful herein have been previously described.

Nonvolatile silicone fluids can also useful as active hair care components in the compositions of the present invention. "Nonvolatile" means that the silicone material has essentially no vapor pressure at one atmosphere, at 25° C. Nonvolatile silicones will generally have a boiling point in excess of about 250° C. and a viscosity in excess of about 10 centipoise at 25° C. Those skilled in the art will recognize that slight vapor pressures may sometimes be measured for some fluids which are not of practical significance in silicone conditioner product formulation. These materials are meant to be included herein as nonvolatile fluids. Examples of such materials include polydimethylsiloxanes (fluids and gums), aminosilicones and phenylsilicones. These include polyalkyl or polyaryl siloxanes with the following structure:

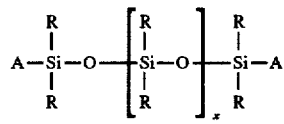

wherein R is alkyl or aryl, and x is an integer from about 7 to about 8,000 may be used. A represents groups which block the ends of the silicone chains.

The alkyl or aryl groups substituted on the siloxane chain (R) or at the ends of the siloxane chains (A) may have any structure as long as the resulting silicones remain fluid at room temperature, are hydrophobic, are neither irritating, toxic nor otherwise harmful when applied to the hair, are compatible with the other components of the composition, are chemically stable under normal use and storage conditions, and are capable of being deposited on and of conditioning hair.

Suitable A groups include methyl, methoxy, ethoxy, propoxy, and aryloxy. The two R groups on the silicone atom may represent the same group or different groups. Preferably, the two R groups represent the same group. Suitable R groups include methyl, ethyl, propyl, phenyl, methylphenyl and phenylmethyl. The preferred silicones are polydimethyl siloxane, polydiethylsiloxane, and polymethylphenylsiloxane. Polydimethylsiloxane is especially preferred.

Silicones useful in the present invention are also commercially available. Suitable examples include Viscasil, a trademark of the General Electric Company and silicones offered by Dow Corning Corporation and by SWS Silicones, a division of Stauffer Chemical Company.

Other useful silicone materials include cationic materials of the formula:

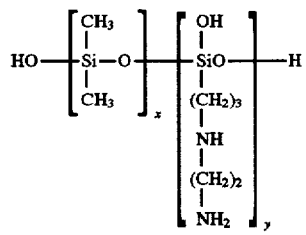

in which x and y are integers which depend on the molecular weight, the average molecular weight being approximately between 5,000 and 10,000. This polymer is also known as "amodimethicone".

Other silicone cationic polymers which can be used in the present composition correspond to the formula:

in which G is chosen from the group consisting of hydrogen, phenyl, OH, $C_1$–$C_8$ alkyl and preferably methyl; a denotes 0 or an integer from 1 to 3, and preferably equals 0;

b denotes 0 or 1 and preferably equals 1; the sum n+m is a number from 1 to 2,000 and preferably from 50 to 150, n being able to denote a number from 0 to 1,999 and preferably from 49 to 149 and m being able to denote an integer from 1 to 2,000 and preferably from 1 to 10;

$R_1$ is a monovalent radical of formula $C_qH_{2q}L$ in which q is an integer from 2 to 8 and L is chosen from the groups —N(R$_2$)CH$_2$—CH$_2$—N(R$_2$)$_2$
—N(R$_2$)$_2$
—N$^+$(R$_2$)$_3$A$^-$
—N$^+$(R$_2$)$_2$CH$_2$—CH$_2$—N$^+$(R$_2$)$_3$A$^-$ in which $R_2$ is chosen from the group consisting of hydrogen, phenyl, benzyl, a saturated hydrocarbon radical, preferably an alkyl radical containing from 1 to 20 carbon atoms, and A$^-$ denotes a halide ion.

These compounds are described in greater detail in European Patent Application EP 95,238. A preferred polymer corresponding to this formula is the polymer known as "trimethylsilylamodimethicone" of formula:

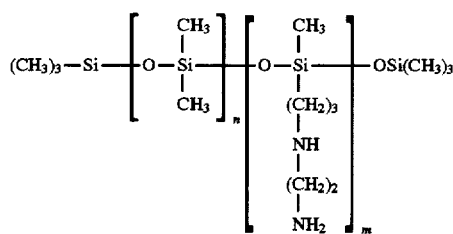

Compositions of the present invention may comprise up to about 1.0% of a trimethylsilyl amodimethicone silicone conditioning material.

Other silicone cationic polymers which can be used in the present compositions correspond to the formula:

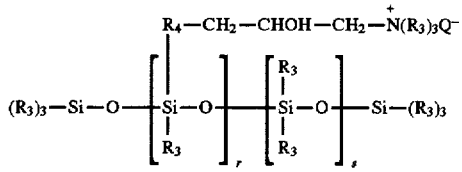

in which $R_3$ denotes a monovalent hydrocarbon radical having from 1 to 18 carbon atoms, and more especially an alkyl or alkenyl radical such as methyl;

$R_4$ denotes a hydrocarbon radical such as, preferably a $C_1$–$C_{18}$ alkylene radical or a $C_1$–$C_{18}$, and preferably $C_1$–$C_{18}$, alkyleneoxy radical;

$Q^-$ is a halide ion, preferably chloride;

r denotes an average statistical value from 2 to 20, preferably from 2 to 8;

s denotes an average statistical value from 20 to 200, and preferably from 20 to 50.

These compounds are described in greater detail in U.S. Pat. No. 4,185,017.

A polymer of this class which is especially preferred is that sold by UNION CARBIDE under the name "UCAR SILICONE ALE 56".

Silicone conditioning agents are optionally used in the present compositions, generally at levels of from about 0.1% to about 18%, preferably from about 0.5% to about 15%.

Preferred silicone conditioning agents for use in the present compositions comprise combinations of volatile silicone fluids having viscosities of less than about 10 centipoise, and from about 0.015% to about 9.0%, preferably from about 0.5% to about 2.0%, of silicone gums having viscosities of greater than about 1,000,000 centipoise, at ratios of volatile fluid to gum of from about 90:10 to about 10:90, preferably from about 85:15 to about 50:50.

Alternative preferable nonvolatile silicone materials for use in the present invention comprise non-volatile silicone fluids having viscosities of less that about 100,000 cP (centipoise), and from about 0.015% to about 9.0%, preferably from about 0.5% to about 2.0%, of silicone gums having viscosities greater than about 1,000,000 cP, especially polydimethylsiloxane gums and polyphenylmethylsiloxane gums, at ratios of non-volatile fluid to gum of from about 70:30 to about 30:70, preferably from about 60:40 to about 40:60.

The efficacy of nonvolatile silicone hair conditioning agents can be enhanced through the use of silicone resins which are mixable with the silicone hair conditioning agent. Silicone resins are highly crosslinked polymeric siloxane systems. The crosslinking is introduced through the incorporation of trifunctional and tetrafunctional silanes with monofunctional or difunctional, or both, monomer units during manufacture of the silicone resin. As is well understood in the art, the degree of crosslinking that is required in order to result in a silicone resin will vary according to the specific silane units incorporated into the silicone resin. In general, silicone materials which have a sufficient level of trifunctional and tetrafunctional siloxane monomer units (and hence, a sufficient level of trifunctional and tetrafunctional siloxane monomer units (and hence, a sufficient level of crosslinking) such that they dry down to a rigid, or hard, film are considered to be silicone resins. The ratio of oxygen atoms to silicon atoms is indicative of the level of crosslinking in a particular silicone material. Silicone resins will generally have at least about 1.1 oxygen atoms per silicon atom. Preferably, the ratio of oxygen:silicon atoms is at least about 1.2:1.0. Typical silanes used in the manufacture of silicone resins ae monomethyl-, dimethyl-, monophenyl-, diphenyl-, methylphenyl-, monovinyl-, and methylvinyl-chlorosilanes, and tetrachlorosilane. Preferred resins are the methyl substituted silicone resins, such as those offered by General Electric as GE SS4230 and SS4267. Commercially available silicone resins will generally be supplied in an unhardened form in a low viscosity volatile or nonvolatile silicone fluid. The silicone resins for use herein should be supplied and incorporated into the present compositions in such non-hardened form rather than as a hardened resin, as will be readily apparent to those skilled in the art.

The weight ratio of the nonvolatile silicone fluid conditioning component to the silicone resin component is preferably from about 4:1 to about 400:1. More preferably such ratio is from about 9:1 to about 200:1, most preferably from about 19:1 to about 100:1, particularly when the silicone fluid component is a polydimethylsiloxane fluid or a mixture of polydimethylsiloxane fluid and polydimethylsiloxane gum, as described above.

Other active hair care materials for use with the vehicle systems of the present invention are silicone polymer materials which provide both style retention and conditioning benefits to the hair. These include silicone polymers that are rigid silicone polymers. Such materials are described in U.S. Pat. No. 4,902,499, Bolich et al., issued Feb. 20, 1990.

Hydrolyzed animal protein hair conditioning agents may also be included in the present compositions. Such materials are present in the compositions at levels of from about 0.1% to about 1.5%. An example of a commercially available material is sold under the tradename Crotein Q® from Croda, Inc.

Combinations of the aforementioned conditioning agents may also be used in the present compositions.

Other optional ingredients include pearlescent aids, such as ethylene glycol distearate (which may also provide a thickening or suspending benefit, and thereby also be included as a component of the carrier system); preservatives, such as benzyl alcohol, methyl paraben, propyl paraben and imidazolidinyl urea; sodium chloride; sodium sulfate; polyvinyl alcohol; ethyl alcohol; pH adjusting agents, such as citric acid, sodium citrate, succinic acid, phosphoric acid, sodium hydroxide, and sodium carbonate; coloring agents, such as any of the FD&C or D&C dyes; hair oxidizing (bleaching) agents, such as hydrogen peroxide, perborate and persulfate salts; hair reducing agents, such as the thioglycolates; anti-dandruff active ingredients; perfumes; sequestering agents, such as disodium ethylenediamine tetra-acetate; glycerin and propylene glycol. Such optional ingredients generally are used individually at levels of from about 0.01% to about 10.0%, preferably from about 0.05% to about 5.0%, of the composition.

The following examples illustrate the present invention. It will be appreciated that other modifications of the present invention within the skill of those in the cosmetic composition formulation art can be undertaken without departing from the spirit and scope of this invention. All parts, percentages, and ratios herein are by weight unless otherwise specified.

EXAMPLE I

The following is a hair styling/conditioning rinse composition representative of the present invention.

| Component | Weight % |
| --- | --- |
| Styling Agent Premix | |
| Silicone Copolymer[1] | 2.00 |
| Phenylpentamethyl disiloxane | 9.00 |
| Diioctyl sebacate | 0.10 |
| Xanthan Premix | |
| Xanthan gum | 0.25 |
| DRO H$_2$O | 25.00 |
| Main Mix | |
| Dihydrogenated tallow-dimethylammonium chloride (DTDMAC) | 0.50 |
| EDTA, disodium salt | 0.10 |
| D.C. 929[2] | 2.00 |
| Perfume | 0.10 |
| Natrosol Plus CS Grade D-67[3] | 0.75 |
| Locust bean gum | 0.75 |
| Kathon CG[4] | 0.04 |
| DRO H$_2$O | q.s. to 100% |

[1]20/60/20 N,N-dimethylacrylamide/isobutyl methacrylate/PDMS macromer (20,000 MW), polymer molecular weight about: 300,000.
[2]Amodimethicone, commercially available from Dow Corning
[3]Hydrophobically modified hydroxethylcellulose having a C$_{16}$ alkyl substitution of from about 0.50% to about 0.95%, by weight, and a hydroxyethyl molar substitution of from about 2.3 to about 3.3, and where the average molecular weight of the hydroxyethyl cellulose prior to substitution is approximately 700,000, available from Aqualon Company.
[4]preservative commercially available from Rohm and Haas The composition is prepared as follows. The DRO (double reverse osmosis) water is first heated to 71° C. The DTDMAC, EDTA, and D.C. 929 are added to the water and mixed for about 5 minutes. The Natrosol is added to the composition with mixing. The Locust Bean Gum is added to the composition with mixing. The composition is then homogenized with a disperser, for example a Gifford-Wood mill, for about 2 minutes. The batch is then cooled to 38° C. The xanthan gum premix, styling agent premix, perfume and Kathan CG are added to the composition with mixing for about 10 minutes. The batch is cooled to ambient temperature and stored.

EXAMPLE II

The following is a hair styling rinse composition representative of the present invention.

| Component | Weight % |
| --- | --- |
| Styling Agent Premix | |
| Silicone Copolymer[1] | 3.00 |
| Phenylpentamethyl disiloxane | 9.00 |
| Hydroxypropylpentamethyl disiloxane | 6.00 |
| Isostearyl alcohol | 1.00 |
| Silicone Gum Premix | |
| Silicone Gum G.E. SE 76[2] | 0.50 |
| Decamethyl cyclopentasiloxane | 4.00 |
| Main Mix | |
| Natrosol Plus CS Grade D-67[3] | 0.60 |
| Locust bean gum | 0.50 |
| EDTA, disodium salt | 0.15 |
| DTDMAC | 0.65 |
| Glydant[4] | 0.40 |
| Perfume | 0.20 |
| DRO H$_2$O | q.s. to 100% |

[1]10/70/20 acrylic acid/n-butyl methacrylate/silicone macromer, the macromer having a molecular weight of about 20,000, prepared in a manner similar to Example C-2c of U.S. Pat. No. 4,728,571, Clemens, issued March 1, 1988, polymer molecular weight about 300,000
[2]Commercially available from General Electric
[3]hydrophobically-modified hydroxyethyl cellulose commercially available from Aqualon Co.
[4]preservative commercially available from Glyco, Inc.

The composition is prepared as follows. The DRO water is heated to 71° C. The DTDMAC, EDTA, and silicone gum premix are added to the water with mixing for about 5 minutes. The Natrosol is added with mixing. The Locust Bean Gum is added with mixing. The composition is then homogenized with a disperser, for example a Gifford-Wood mill, for about 2 minutes. The batch is cooled to 38° C. and the styling agent premix, the perfume and the Glydant are added with mixing for about 10 minutes. The batch is cooled to ambient temperature and stored.

EXAMPLE III

The following is a hair styling rinse composition representative of the present invention.

| Component | Weight % |
| --- | --- |
| Natrosol Plus CS Grade D-67[1] | 1.20 |
| Xanthan Gum | 0.25 |
| Citric Acid | 0.073 |
| Sodium Citrate | 0.175 |
| Kathon CG | 0.033 |
| DiTallow DiMethyl Ammonium Chloride (DTDMAC) | 0.75 |
| Hydrogenated Tallow Betaine | 0.33 |
| Styling Agent Premix | |
| T-Butyl Acrylate/PDMS Copolymer (10,000 MW - 80/20 W/W) | 2.50 |
| Phenethyl Pentamethyl Disiloxane | 1.875 |
| Diisodecyl adipate | 0.70 |
| D4 Cyclomethicone | 5.625 |
| Polydimethyl Siloxane Gum/ D5 Cyclomethicone Premix (15/85)[2] | 2.333 |
| Perfume | q.s. |
| DRO Water | q.s. to 100% |

[1]Hydrophobically modified hydroxyethyl cellulose available from Aqualon Corp.
[2]G.E. SE-76 gum available from G.E. Silicones The composition is prepared as follows. The xanthan gum is first slurried in water at 4% xanthan gum, until fully hydrated. In a separate vessel the copolymer is mixed into the phenethyl pentamethyl disiloxane and D4 cyclomethicone.

The remaining water is preheated to about 71° C. The DTDMAC, citric acid, sodium citrate, and hydrogenated tallow betaine are added to the water and mixed until melted. This mixture is then cooled to about 38° C. The Natrosol Plus, silicone gum premix, Kathon and perfume are added and mixed until homogeneous. This mixture is then cooled to about 38° C. The xanthan gum premix and copolymer premix are then added and the mixture is agitated until homogeneous. The resulting composition is cooled to ambient temperature.

EXAMPLE IV

The following is a hair styling conditioner composition which is representative of the present invention.

| Component | Wt. % |
|---|---|
| Disodium EDTA | 0.10 |
| Monosodium Phosphate | 0.08 |
| Disodium Phosphate | 0.02 |
| Tallow Diethanol Amide | 0.60 |
| Natrosol Plus CS Grade D-67[1] | 1.50 |
| Glydant | 0.37 |
| Perfume | 0.02 |
| DRO Water | q.s. to 100% |
| Styling Polymer Premix | |
| Styling Polymer[2] | 3.00 |
| Phenyl Pentamethyl Disiloxane | 4.95 |
| Octamethyl Cyclotetrasiloxane | 4.05 |
| Tri-n-butyl citrate | 0.30 |
| Silicone Gum Premix | |
| G.E. SE 76[3] | 0.75 |
| Octamethyl Cyclotetrasiloxane | 4.25[1] |

[1]Hydrophobically modified hydroxyethylcellulose available from Aqualon
[2]Isobutylmethacrylate/2-ethylhexylmethacrylate/N,N-dimethyl-acrylamide copolymer 80/5/15
[3]Silicone Gum available from General Electric The composition is prepared as follows. The DRO water is first heated to 71° C. The EDTA, tallow diethanolamide, mono- and disodium phosphate are added with mixing for about 5 minutes. The Natrosol is added with mixing. The batch is cooled to 38° C. The Silicone Gum premix is added with mixing. The composition is then homogenized using a disperser, e.g., a Gifford-Wood mill, for about 2 minutes. The batch is cooled to 38° C. The perfume, Styling Polymer Premix and Glydant are added with mixing for about 10 minutes. The batch is cooled to ambient temperature and stored.

EXAMPLE V

The following is a hair styling conditioner composition which is representative of the present invention.

| Component | Wt. % |
|---|---|
| Disodium EDTA | 0.15 |
| Monosodium Phosphate | 0.04 |
| Disodium Phosphate | 0.12 |
| Dihydrogenated tallow dimethyl ammonium chloride (DTDMAC) | 0.75 |
| Locust Bean Gum | 0.70 |
| Xanthan Gum | 0.25 |
| Natrosol Plus CS Grade D-67[1] | 0.70 |
| Glydant | 0.37 |
| Perfume | 0.02 |
| Water | q.s. to 100% |

| Component | Wt. % |
|---|---|
| Silicone Gum Premix | |
| G.E. SE 76[2] | 0.50 |
| Octamethyl Cyclotetrasiloxane | 3.00 |
| Styling Polymer Premix | |
| Styling Polymer[3] | 3.00 |
| Dimethicone copolyol[4] | |
| Phenyl Pentamethyl Disiloxane | 9.00 |
| Hydroxypropyl Pentamethyl Disiloxane | 6.00 |

[1]Hydrophobically modified hydroxyethylcellulose available from Aqualon
[2]Silicone Gum available from General Electric
[3]Isobutylmethacrylate/2-ethylhexylmethacrylate/N,N-dimethyl-acrylamide copolymer 80/5/15
[4]D.C. 1248, available commercially from Dow Corning (Midland, Michigan, U.S.A.).

The composition is prepared as follows. The DRO water is heated to 71° C. The DTDMAC, disodium EDTA, monosodium phosphate, and disodium phosphate are added and the composition is mixed for about 5 minutes. The silicone gum premix, locust bean gum, xanthan gum and Natrosol are added with mixing. The composition is then homogenized using a disperser, e.g., a Gifford-Wood Mill, for about 2 minutes. The batch is cooled to 38° C. and the Xanthan Gum premix, styling polymer premix, perfume and Glydant are added and mixed for about 10 minutes. The composition is then cooled to ambient temperature and stored.

EXAMPLE VI

The following is a hair styling rinse composition representative of the present invention.

| Component | Weight % |
|---|---|
| Natrosol Plus - Grade 330 | 2.0 |
| Hydrogenated Tallow Betaine | 0.30 |
| DiTallow DiMethyl Ammonium Chloride (DTDMAC) | 0.75 |
| Citric Acid | 0.07 |
| Sodium Citrate | 0.17 |
| Styling Polymer Premix - | |
| Styling Polymer[2] | 2.5 |
| Phenyl Ethyl Pentamethyl Disiloxane | 1.875 |
| Octamethyl Cyclotetrasiloxane | 5.625 |
| Camphor | 0.30 |
| Silicone Gum Premix - | |
| Polydimethyl Siloxane Gum[3] | 0.35 |
| Decamethyl Cyclopentasiloxane | 1.98 |
| Kathon CG | 0.033 |
| Perfume | 0.2 |
| Xanthan Gum[4] | 0.25 |
| DRO Water | q.s. to 100% |

[1]Hydrophobically modified hydroxyethyl cellulose available from Aqualon Corp.
[2]80/20 t-Butylacrylate/PDMS macromer, the macromer having a molecular weight of about 10,000, prepared in a manner similar to Example C-2b of U.S. Pat. No. 4,728,571, Clemens, issued March 1, 1988
[3]S.E.-76 gum available from General Electric
[4]Readily dispersible xanthan gum The composition is prepared as follows.

The styling polymer premix is prepared by combining the styling polymer, phenyl ethyl pentamethyl disiloxane, and the octamethyl cyclotetrasiloxane.

The silicone gum premix is prepared by combining, in a separate vessel and mixing the silicone gum and the decamethyl cyclopenta siloxane until homogeneous.

About one-half of the DRO water is first heated to about 66° C. The hydrogenated tallow betaine, citric acid, and sodium citrate are added and mixed until homogeneous. The Natrosol and xanthan gum are added and mixed until homogeneous. The composition is cooled to about 38° C. The styling polymer premix, Kathon CG and perfume are added. The composition is mixed and homogenized with a homogenizer such as a Tekmar homogenizer (preferably in-line).

The remaining DRO water is heated to about 88° C., the DTDMAC is added and mixed until homogeneous. The mixture is then cooled to about 43° C. The silicone gum premix is added and the composition homogenized with a homogenizer (in-line preferred).

The two premixes are then combined and mixed until homogeneous to form the styling rinse composition.

EXAMPLE VII

The following is a hair styling/conditioner composition representative of the present invention.

| Component | Weight % |
|---|---|
| Citric Acid | 0.08 |
| Sodium Citrate | 0.20 |
| Behenyl Alcohol | 1.40 |
| Stearalkonium Chloride | 0.30 |
| Perfume | 0.20 |
| Kathon CG (preservative C) | 0.03 |
| Styling Polymer Premix | |
| Styling Polymer[1] | 2.00 |
| Octamethyl Cyclotetrasiloxane | 5.00 |
| Pentamethyl Cyclopentasiloxane | 5.00 |
| Butyl Stearate | 0.30 |
| Trimethylsilylamodimethicone[2] | 0.05 |
| Distearyl Dimethyl Ammonium Chloride | 0.15 |
| DRO Water | 9.5 |
| | Q.S. to 100% |

[1]80/20 t-Butylatrylate/PDMS macromer, the macromer having a molecular weight of about 10,000, prepared in a manner similar to Example C-2b of U.S. Pat. No. 4,728,571, Clemens, issued March 1, 1988
[2]Q2-8220 offered by Dow Corning (Midland, Michigan).

All the ingredients except styling polymer premix, Kathon, and perfume are mixed together and heated to 82° C. for one-half hour. The batch is then cooled to about 50° C. while being mixed with a high shear mixer. The remaining ingredients are added and the batch is cooled to ambient temperature while continuing with the high shear mixing.

EXAMPLES VIII-IX

The following are hair styling/conditioning rinse compositions representative of the present invention.

| Component | VIII | IX |
|---|---|---|
| Citric Acid | 0.02 | 0.02 |
| Sodium Citrate | 0.09 | 0.09 |
| Cetyl Alcohol | 0.12 | 0.12 |
| Stearyl Alcohol | 0.08 | 0.08 |
| Natrosol Plus CS Grade D-67[1] | 1.25 | 1.40 |
| Xanthan Gum[2] | 0.25 | 0.25 |
| Styling Polymer Premix | | |
| Styling Polymer[3] | 1.75 | 1.75 |
| Octamethyl Tetrasiloxane | 5.98 | 5.98 |
| Decamethyl Pentasiloxane | 2.56 | 2.56 |
| Butyl Stearate | 0.15 | 0.15 |
| Kathon CG | 0.03 | 0.03 |
| Perfume | 0.33 | 0.33 |
| Thickener Premix | | |
| DRO Water | 11.67 | 11.90 |
| Adogen 470 | 0.67 | 1.33 |
| Kemamine ® BQ-2802C | 0.33 | — |
| Silicone Gum Premix | | |
| Decamethyl Pentasiloxane | 1.98 | 1.42 |
| Polydimethyl Siloxane Gum[4] | 0.35 | 0.25 |
| Amodimethicone (Dow Corning Q2-8220) | — | 0.10 |
| DRO Water | Q.S. to 100 | Q.S. to 100 |

[1]Hydrophobically modified hydroxyethyl cellulose from Aqualon Corp.
[2]Readily dispersible xanthan gum
[3]80/20 t-butylacrylate/PDMS macromer, the macromer having a molecular weight of about 10,000, prepared in a manner similar to Example C-2b of U.S. Pat. No. 4,728,571, Clemens, issued March 1, 1988
[4]SE-76 gum available from General Electric The styling polymer is prepared by combining the styling polymer, the octamethyl tetrasiloxane and decamethyl pentasiloxane and butyl stearate.

The silicone gum premix is prepared by combining and decamethyl pentasiloxane until homogeneous.

The thickener premix is prepared by combining and mixing (in a separate vessel) DRO water, any primary and secondary thickeners (premelted), the silicone gum premix, and any other optional silicones, at 71° C., until homogeneous.

In another vessel, the DRO water is heated to 71° C. Citric acid, sodium citrate, cetyl alcohol, stearyl alcohol and Natrosol Plus CS grade D-67 are added an mixed till homogeneous. The xanthan gum is added and mixed till homogeneous. The styling polymer premix, Kathon CG and perfume are added and mixed till homogeneous. The composition is further dispersed with an in-line homogenizer (such as a Tekmar homogenizer) and then cooled to 37° C.

The thickener premix is also further dispersed with an in-line homogenizer and cooled to 38° C. and added to the final vessel, mixing until homogeneous to form the styling rinse composition.

What is claimed:

1. A hair care composition comprising:
   (a) a hair styling/conditioning component comprising:
      (i) from about 0.1% to about 10%, by weight of the composition, of a silicone macromer-containing hair styling/conditioning copolymer, said silicone macromer, molecular weight (weight average) of from about 1,000 to about 50,000, covalently bonded to a nonsilicone organic polymer backbone or organic oligomeric portion of a polymeric backbone, said copolymer having a molecular weight of from about 200,000 to about 1,000,000 and a Tg of at least about −20° C.;
      (ii) from about 0.1% to about 99.7%, by weight of the composition, of volatile solvent in which said copolymer is soluble or dispersible, said volatile solvent being a volatile silicone fluid which is immiscible in water, wherein said copolymer is solubilized or dispersed in said volatile silicone fluid to provide a copolymer-volatile solvent solution, and wherein, when said solution is dried, the copolymer separates into a discontinuous phase which includes the silicone macromer and a continuous phase which includes the nonsilicone organic polymer backbone or organic oligomeric portion; and
      (iii) a nonvolatile plasticizer that is safe for topical application to the hair and skin of humans, wherein said composition has a plasticizer:copolymer weight ratio of from about 1:20 to about 1:1 and said plasticizer is miscible with said copolymer-volatile solvent solution and has a solubility parameters, δ, of between about 7 and about 10 (calories/cc)$^{1/2}$; and (b) from about 65% to about 99.7% of an additional carrier vehicle which is water.

2. A hair care composition as in claim 1, wherein said composition comprises from about 65% to about 98% of said additional carrier.

3. A hair care composition as in claim 2, wherein said additional carrier further comprises: a) from about 0.1% to about 10%, by weight of the composition, of a lipid vehicle material and from about 0.05% to about 5%, by weight of the composition, of a cationic surfactant; or b) from about 0.1% to about 10% of a hydrophobically modified nonionic water-soluble polymer which comprises a water-soluble polymer backbone and hydrophobic groups selected from the group consisting of $C_8$–$C_{22}$ alkyl, aryl alkyl, alkyl aryl groups and mixtures thereof; wherein the ratio of the hydrophilic portion to the hydrophobic portion of the polymer is from about 10:1 to about 1000:1; and b) from about 0.3% to about 5.0% by weight of the composition of a water-soluble surfactant, a water-insoluble surfactant, a water-soluble polymeric thickener having a molecular weight greater than about 20,000, or a mixture thereof wherein said composition contains no more than about 1.0%, by weight, of water soluble surfactants.

4. A composition as in claim 1, wherein the plasticizer:copolymer weight ratio is from about 1:5 to about 1:2.

5. A composition as in claim 4, wherein said plasticizer:copolymer weight ratio is from 1:12 to about 1:2.5.

6. A composition as in claim 1, wherein said plasticizer is selected from the group consisting of adipates, phthalates, isophthalates, azelates, stearates, citrates, trimellitates, silicone copolyols, iso $C_{14}$–$C_{22}$ alcohols, methyl alkyl silicones, carbonates, sebacates, isobutyrates, oleates, phosphates, myristates, ricinoleates, pelargonates, valerates, oleates, camphor, and castor oil.

7. A composition as in claim 6, wherein said plasticizer is selected from the group consisting of diisobutyl adipate, bis(2-ethylhexyl) adipate, diisodecyl adipate, bis(2-butoxyethyl) adipate, di-n-hexyl adipate, dibutyl phthalate, butyl octyl phthalate, di-n-octyl phthalate, diisooctyl phthalate, bis(2-ethylhexyl) phthalate, n-octyl n-decyl phthalate, di-n-hexyl phthalate, isooctyl isodecyl phthalate, diisodecyl phthalate, ditridecyl phthalate, butyl cyclohexyl phthalate, diisoctyl benzyl phthalate, butyl benzyl phthalate, dicyclohexyl phthalate, diphenyl phthalate, isodecyl benzyl phthalate, bis(2-butoxyethyl) phthalate, bis(2-ethylhexyl) isophthalate, diisooctyl benzyl phthalate, di(2-ethylhexyl) azelate, bis(2-ethylhexyl) azelate, n-butyl stearate, butyl acetoxystearate, butoxyethyl, stearateacetyl tri-n-butyl citrate, tri-n-butyl citrate, and acetal tri-2-ethyl hexyl citrate, tri-(2-ethylhexyl) trimellitate, triisooctyl trimellitate, dibutyl carbonate, butyl oleate, n-butyl, butyrate, isobutyl butyrate, isopropyl butyrate, dibutyl carbonate, ethyl palmitate, isooctyl palmitate, methyl ricinoleate, butyl ricinoleate, diisooctyl sebacate, triisobutyl phosphate, isodecy pelargonate, ethyl valerate, isocetyl alcohol, octododecanol, isopropyl myristate, isostearyl alcohol, silicone copolyols, methyl alkyl silicones having $C_2$–$C_{20}$ alkyl and from 1 to about 500 siloxane monomer units, and mixtures thereof.

8. A composition as in claim 7, wherein said plasticizer is butyl stearate, butyl oleate, triisobutyl phosphate, isodecyl pelargonate, ethyl palmitate, dibutyl carbonate, castor oil, ditridecyl phthalate, methyl ricinoleate, butyl ricinoleate, diisooctyl sebacate, camphor, ethyl valerate, isostearyl alcohol and cetyl alcohol or methyl alkyl silicone, or a mixture thereof.

9. A hair care composition as in claim 1, wherein said hair styling/conditioning copolymer comprises a copolymer, having a molecular weight of from about 10,000 to about 1,000,000, which has a vinyl polymeric backbone having grafted to it monovalent siloxane polymeric moieties, said copolymer comprising C monomers and components selected from the group consisting of A monomers, B monomers, and mixtures thereof, wherein:

A is at least one free radically polymerizable vinyl monomer, the amount by weight of A monomer, when used, being up to about 98% by weight of the total weight of all monomers in said copolymer;

B is at least one reinforcing monomer copolymerizable with A, the amount by weight of B monomer, when used, being up to about 98% of the total weight of all monomers in said copolymer, said B monomer being selected from the group consisting of polar monomers and macromers; and C is a polymeric monomer having a molecular weight of from about 1,000 to about 50,000 and the general formula

wherein

X is a vinyl group copolymerizable with the A and B monomers

Y is a divalent linking group

R is a hydrogen, lower alkyl, aryl or alkoxy

Z is a monovalent siloxane polymeric moiety having a number average molecular weight of at least about 500, is essentially unreactive under copolymerization conditions, and is pendant from said vinyl polymeric backbone after polymerization n is 0 or 1, and m is an integer from 1 to 3 wherein C comprises from about 0.01% to about 50% of the copolymer.

10. A hair care composition as in claim 9, wherein said composition comprises from about 65% to about 98% of said additional carrier.

11. A hair care composition as in claim 10, wherein said additional carrier further comprises: a) from about 0.1% to about 10%, by weight of the composition, of a lipid vehicle material and from about 0.05% to about 5%, by weight of the composition, of a cationic surfactant; or b) from about 0.1% to about 10% of a hydrophobically modified nonionic water-soluble polymer which comprises a water-soluble polymer backbone and hydrophobic groups selected from the group consisting of $C_8$–$C_{22}$ alkyl, aryl alkyl, alkyl aryl groups and mixtures thereof; wherein the ratio of the hydrophilic portion to the hydrophobic portion of the polymer is from about 10:1 to about 1000:1; and b) from about 0.3% to about 5.0% by weight of the composition of a water-soluble surfactant, a water-insoluble surfactant, a water-soluble polymeric thickener having a molecular weight greater than about 20,000, or a mixture thereof wherein said composition contains no more than about 1.0%, by weight, of water soluble surfactants.

12. A composition as in claim 11, wherein the plasticizer:copolymer weight ratio is from about 1:15 to about 1:2.

13. A composition as in claim 12, wherein said plasticizer:copolymer weight ratio is from about 1:12 to about 1:2.5.

14. A composition as in Claim 13, wherein said plasticizer is selected from the group consisting of adipates, phthalates, isophthalates, azelates, stearates, citrates, trimellitates, silicone copolyols, iso $C_{14}$–$C_{22}$ alcohols, methyl alkyl silicones, carbonates, sebacates, isobutyrates, oleates, phosphates, myristates, ricinoleates, pelargonates, valerates, oleates, camphor, and castor oil.

15. A composition as in claim 14, wherein said plasticizer is selected from the group consisting of diisobutyl adipate, bis(2-ethylhexyl) adipate, diisodecyl adipate, bis(2-butoxyethyl) adipate, di-n-hexyl adipate, dibutyl phthalate, butyl octyl phthalate, di-n-octyl phthalate, diisooctyl phthalate, bis(2-ethylhexyl) phthalate, n-octyl n-decyl phthalate, di-n-hexyl phthalate, isooctyl isodecyl phthalate, diisodecyl phthalate, ditridecyl phthalate, butyl cyclohexyl phthalate, diisoctyl benzyl phthalate, butyl benzyl phthalate, dicyclohexyl phthalate, diphenyl phthalate, isodecyl benzyl phthalate, bis(2-butoxyethyl) phthalate, bis(2-ethylhexyl) isophthalate, diisooctyl benzyl phthalate, di(2-ethylhexyl) azelate, bis(2-ethylhexyl) azelate, n-butyl stearate, butyl acetoxystearate, butoxyethyl, stearateacetyl tri-n-butyl citrate, tri-n-butyl citrate, and acetal tri-2-ethyl hexyl citrate, tri-(2-ethylhexyl) trimellitate, triisooctyl trimellitate, dibutyl carbonate, butyl oleate, n-butyl, butyrate, isobutyl butyrate, isopropyl butyrate, dibutyl carbonate, ethyl palmitate, isooctyl palmitate, methyl ricinoleate, butyl ricinoleate, diisooctyl sebacate, triisobutyl phosphate, isodecy pelargonate, ethyl valerate, isocetyl alcohol, octododecanol, isopropyl myristate, isostearyl alcohol, silicone copolyols, methyl alkyl silicones having $C_2$–$C_{20}$ alkyl and from 1 to about 500 siloxane monomer units, and mixtures thereof.

16. A hair care composition as in claim 9, wherein said carrier further comprises:
   (a) from about 0.1% to about 10%, by weight of the composition, of a hydrophobically modified nonionic water-soluble polymer which comprises a water-soluble polymer backbone and hydrophobic groups selected from the group consisting of $C_8$–$C_{22}$ alkyl, aryl alkyl, alkyl aryl groups and mixtures thereof; wherein the ratio of the hydrophilic portion to the hydrophobic portion of the polymer is from about 10:1 to about 1000:1; and
   (b) from about 0.3% to about 5.0% by weight of the composition of a water-soluble surfactant, a water-insoluble surfactant, a water-soluble polymeric thickener having a molecular weight greater than about 20,000, or a mixture thereof;
   wherein said compositions comprise no more than about 1.0% of water-soluble surfactants.

17. A composition as in claim 9, wherein said volatile solvent is cyclic or linear polydimethylsiloxane.

18. A composition as in claim 17, wherein said copolymer comprises from about 50% to about 90% monomer A, from about 7.5% to about 80% monomer B, and from about 2% to about 25% monomer C.

19. A composition as in claim 18, wherein monomer A is selected from the group consisting of acrylic acid esters of $C_1$–$C_{18}$ alcohols, methacrylic acid esters of $C_1$–$C_{18}$ alcohols, styrene, vinyl acetate, vinyl chloride, vinylidene chloride, acrylonitrile, alpha-methylstyrene, t-butylstyrene, butadiene, cyclohexadiene, ethylene, propylene, vinyl toluene, polystyrene macromer, and mixtures thereof and monomer B is selected from the group consisting of acrylic acid, methacrylic acid, N,N-dimethylacrylamide, dimethylaminoethyl methacrylate, quaternized dimethylaminoethyl methacrylate, methacrylonitrile, methacryloamide, maleic anhydride, half esters of maleic anhydride, itaconic acid, acrylamide, acrylate alcohols, hydroxyethyl methacrylate, diallyldimethyl ammonium chloride, vinyl pyrrolidone, vinyl ethers, maleimides, 2-ethyl-2-oxazoline, vinyl pyridine, vinyl imidazole, styrene sulfonate, and mixtures thereof.

20. The composition of claim 19 wherein the copolymer has a molecular weight of from about 300,000 to about 800,000 and is selected from the group consisting of acrylic acid/n-butylmethacrylate/polydimethylsiloxane macromer; N,N-dimethylacrylamide/ isobutyl methacrylate/ polydimethylsiloxane macromer; dimethylaminoethyl methacrylate/isobutyl methacrylate/2-ethylhexyl methacrylate/polydimethylsiloxane macromer; dimethylaminoethyl methacrylate/isobutyl methacrylate/ polydimethylsiloxane macromer; quaternized dimethylaminoethyl methacrylate/isobutyl methacrylate/ polydimethylsiloxane macromer; acrylic acid/isopropyl methacrylate/polydimethylsiloxane macromer; N,N-dimethylacrylamide/methoxyethyl methacrylate/ polydimethylsiloxane macromer; t-butylacrylate/t-butylmethacrylate/polydimethylsiloxane macromer; t-butylacrylate/N,N-dimethylacrylamide/ polydimethylsiloxane macromer; t-butyl acrylate/acrylic acid/polydimethylsiloxane macromer; and mixtures thereof.

21. The composition of claim 20, wherein said molecular weight is from about 400,000 to 600,000.

22. A hair care composition comprising:
   (a) a hair styling/conditioning component comprising:
      (i) from about 0.1% to about 10%, by weight of the composition of a silicone macromer-containing hair styling/conditioning copolymer, said silicone macromer, molecular weight (weight average) of from about 1,000 to about 50,000, covalently bonded to a nonsilicone organic polymer backbone or organic oligomeric portion of a polymeric backbone, said copolymer having a TG of at least about –20° C.;
      (ii) from about 0.1% to about 99.7%, by weight of the composition, of volatile solvent in which said copolymer is soluble or dispersible, said volatile solvent being a volatile silicone fluid which is immiscible in water, wherein said copolymer is solubilized or dispersed in said volatile silicone fluid to provide a copolymer-volatile solvent solution, and wherein, when said solution is dried, the copolymer separates into a discontinuous phase which includes the silicone macromer and a continuous phase which includes the nonsilicone organic polymer backbone or organic oligomeric portion; and
      (iii) a nonvolatile plasticizer that is safe for topical application to the hair and skin of humans, wherein said composition has a plasticizer:copolymer weight ratio of from about 1:20 to about 1:1, and said plasticizer is miscible with said copolymer-volatile solvent solution and has a solubility parameters, δ, of between about 7 and about 10 (calories/cc)$^{1/2}$; and
   (b) from about 65% to about 99.7% of an additional carrier vehicle which is water.

* * * * *